(12) United States Patent
Waduge et al.

(10) Patent No.: US 10,550,487 B2
(45) Date of Patent: Feb. 4, 2020

(54) LOW NOISE ULTRATHIN FREESTANDING MEMBRANES COMPOSED OF ATOMICALLY-THIN 2D MATERIALS

(71) Applicant: Northeastern University, Boston, MA (US)

(72) Inventors: Pradeep Waduge, East Boston, MA (US); Swastik Kar, Belmont, MA (US); Meni Wanunu, Boston, MA (US); Joseph Larkin, Dorchester, MA (US); Ismail Bilgin, Los Alamos, NM (US)

(73) Assignee: Northeastern University, Boston, MA (US)

( * ) Notice: Subject to any disclaimer, the term of this patent is extended or adjusted under 35 U.S.C. 154(b) by 154 days.

(21) Appl. No.: 15/552,373

(22) PCT Filed: Nov. 25, 2015

(86) PCT No.: PCT/US2015/062686
§ 371 (c)(1),
(2) Date: Aug. 21, 2017

(87) PCT Pub. No.: WO2016/133570
PCT Pub. Date: Aug. 25, 2016

(65) Prior Publication Data
US 2018/0038001 A1    Feb. 8, 2018

Related U.S. Application Data

(60) Provisional application No. 62/119,675, filed on Feb. 23, 2015, provisional application No. 62/118,795, filed on Feb. 20, 2015.

(51) Int. Cl.
*C25B 9/10* (2006.01)
*G01N 33/487* (2006.01)
(Continued)

(52) U.S. Cl.
CPC .............. *C25B 9/10* (2013.01); *C01B 32/186* (2017.08); *C12Q 1/6869* (2013.01);
(Continued)

(58) Field of Classification Search
None
See application file for complete search history.

(56) References Cited

U.S. PATENT DOCUMENTS

2010/0140470 A1    6/2010    Shachal
2011/0171427 A1*   7/2011    Kim ...................... B82Y 30/00
                                                                428/152
(Continued)

FOREIGN PATENT DOCUMENTS

WO    20150077751 A1    5/2015

OTHER PUBLICATIONS

Lee et al., Advanced Materials, vol. 24, No. 17, 2012, pp. 2320-2325. (Year: 2012).*
(Continued)

*Primary Examiner* — Eli S Mekhlin
(74) *Attorney, Agent, or Firm* — Verill Dana, LLP

(57) ABSTRACT

The invention provides methods for direct growth of low noise, atomically thin freestanding membranes of two-dimensional monocrystalline or polycrystalline materials, such as transition metal chalcogenides including molybdenum disulfide. The freestanding membranes are directly grown over an aperture by reacting two precursors in a chemical vapor deposition process carried out at atmospheric pressure. Membrane growth is preferentially over apertures in a thin sheet of solid state material. The resulting membranes are one or a few atomic layers thick and essentially free of defects. The membranes are useful for sequencing of biopolymers through nanopores.

21 Claims, 12 Drawing Sheets

(51) Int. Cl.
  *C01B 32/186*  (2017.01)
  *C12Q 1/6869*  (2018.01)
  *G01N 27/447*  (2006.01)

(52) U.S. Cl.
  CPC ... *G01N 27/4473* (2013.01); *G01N 27/44791* (2013.01); *G01N 33/48721* (2013.01)

(56) References Cited

U.S. PATENT DOCUMENTS

| | | | |
|---|---|---|---|
| 2012/0088235 A1 | 4/2012 | Kokoris et al. | |
| 2013/0256210 A1 | 10/2013 | Fleming | |
| 2013/0309776 A1* | 11/2013 | Dmdic | G01N 27/26 436/94 |
| 2014/0245946 A1* | 9/2014 | Kong | C30B 25/186 117/95 |
| 2015/0020610 A1* | 1/2015 | Hurst | G01L 1/146 73/862.68 |

OTHER PUBLICATIONS

Liu, Ke et al. "Atomically Thin Molybdenum Disulfide Nanopores with High Sensitivity for DNA Translocation", American Chemical Society, 2014, vol. 8, No. 3, pp. 2504-2511 doi: 10.1021/nn406102h.

Waduge, Pradeep et al. "Programmed Synthesis of Freestanding Graphene Nano-Membrane Arrays", Small, 2015, vol. 11, Issue 5, pp. 597-603 doi: 10.1002/sml.201402230.

Waduge, Pradeep et al. "Direct and Scalable Deposition of Atomically Thin Low-Noise MoS2 Membranes on Apertures", American Chemical Society, 2015; pp. A-H doi: 10.1021/acsnano.5b02369.

Feng, J et al. "Identification of Single Nucleotides in MoS2 Nanopores", Nature Nanotechnology, 2015 Manuscript 24 pages, 4 Figures Supporting Information 24 pages, 12 Figures, 2 Tables (48 pages total). doi: 10.1038/nnano.2015.219 arXiv:1505.01608.

Feng, J. et al. "Electrochemical Reaction in Single Later MoS2: Nanopores Opened atom by atom", Nano Letters, 2015, Washington, Amer Chemical Soc., ISSN:1530-6992, pp. 1-39. DOI: 10.1021/acs.nanolett.5b00768.

Sun, L. et al. "Laminar MoS2 membranes for molecule separation", Chem. Commun., 2013, vol. 49, pp. 10718-10720 doi: 10.1039/c3cc46136j.

Wang, X. et al., "Chemical Vapor Deposition Growth of Crystalline Monolayer MoSe2", Amer. Chem. Soc. Nano 2014, vol. 8, No. 5, pp. 5125-5131 DOI: 10.1021/nn501175k.

* cited by examiner

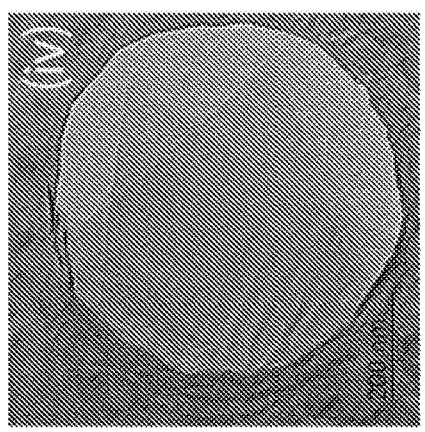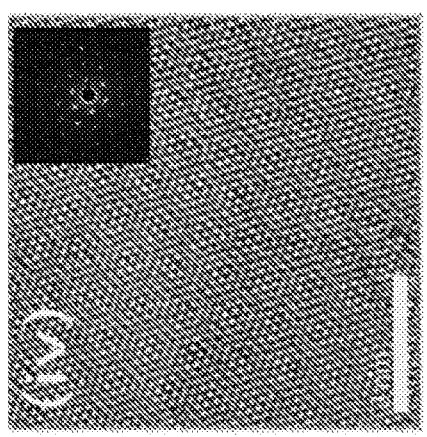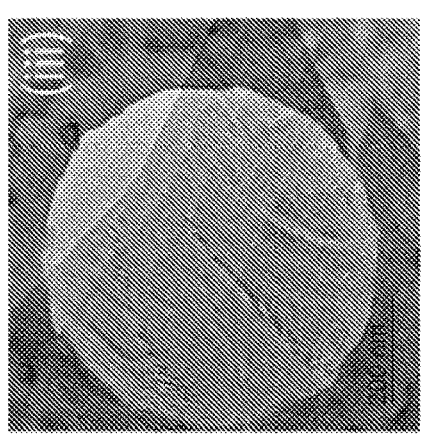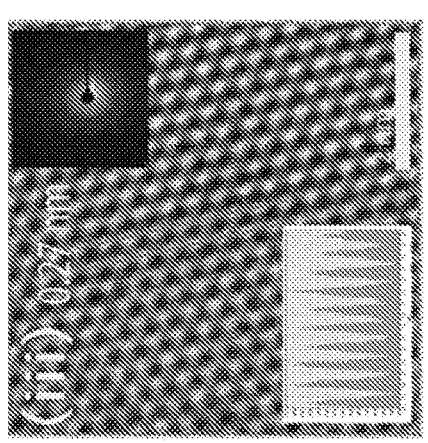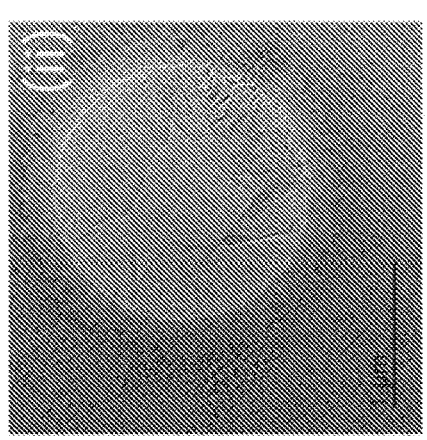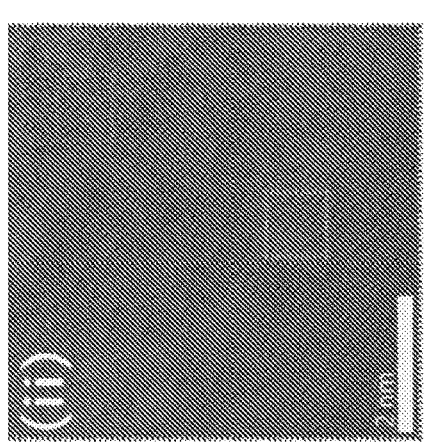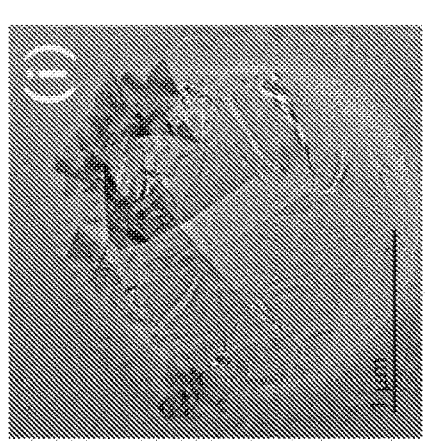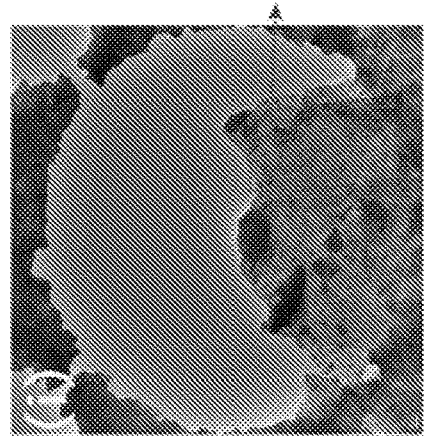
FIG. 2A
FIG. 2B

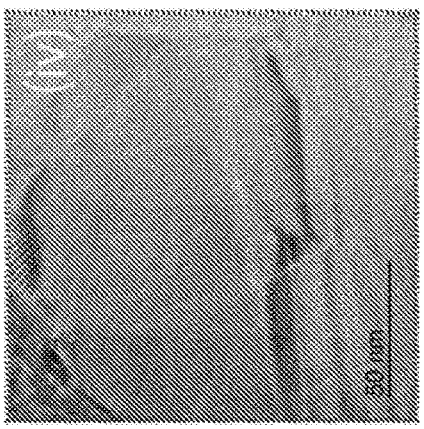
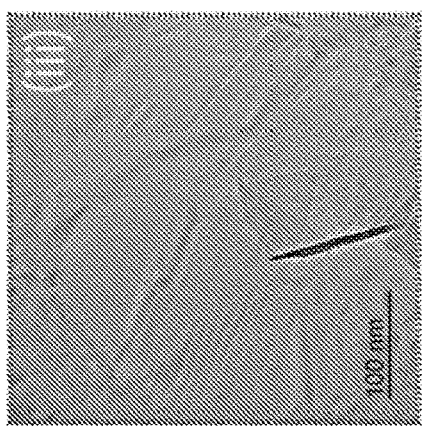
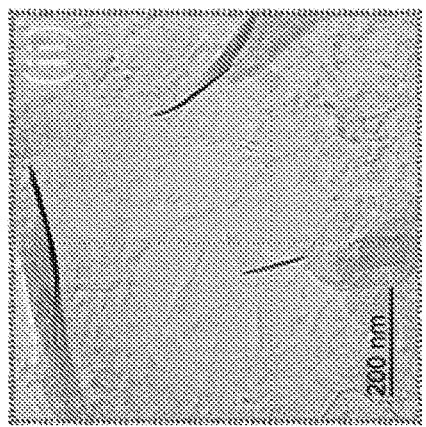
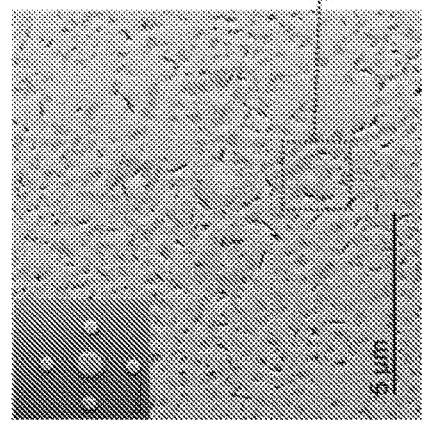
FIG. 2C
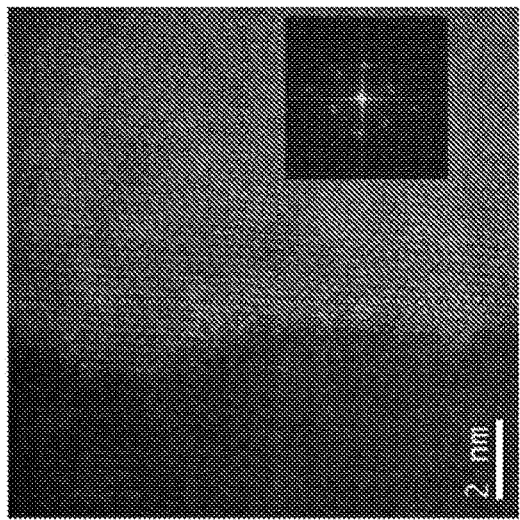
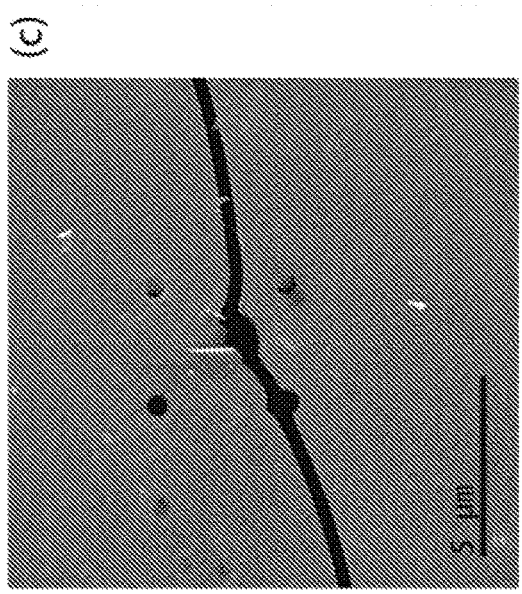
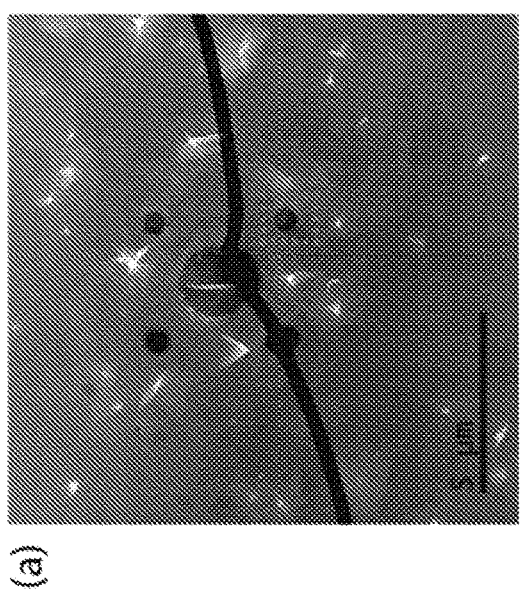
FIG. 3A  FIG. 3B  FIG. 3C

LOW NOISE ULTRATHIN FREESTANDING MEMBRANES COMPOSED OF ATOMICALLY-THIN 2D MATERIALS

This application claims the priority of U.S. Provisional Application Nos. 62/118,795 filed 20 Feb. 2015 and entitled "Aperture-Limited Fabrication of Freestanding MoS₂ Membranes" and 62/119,675 filed 23 Feb. 2015 and entitled "Aperture-Limited Fabrication of Freestanding MoS₂ Membranes". Both provisional applications are hereby incorporated by reference in their entirety.

BACKGROUND

The ability to exfoliate single- and few-layer graphene flakes from bulk graphite opened up new avenues into the physics of two-dimensional materials. [1,2] Even though graphene is a good electrical and thermal conductor, its zero band gap property hinders the possibilities in a wide range of potential applications in next generation nanoelectronics and optoelectronics. [3] Moreover, engineering a band gap of graphene makes the fabrication more complicated and reduces the electronic mobility. [4,5] In this regard, molybdenum disulfide ($MoS_2$), a layered transition metal dichalcogenide (TMDC), in which unsaturated d-electron interactions can give rise to new interesting material properties, has garnered a great interest in many next generation nanotechnology applications due to its fascinating electrical, optical and mechanical properties. [6] $MoS_2$, a semiconductor with a finite band gap, is composed of covalently bonded S—Mo—S sheets that are bound by weak van der Waals forces. The band gap of $MoS_2$ can be tuned from direct (~1.8 eV) [7] to indirect (~1.0 eV) [8] in its bulk and monolayer forms, respectively. It has been investigated that the band structure and band gap of $MoS_2$ are strongly affected by quantum confinement due to its atomically thin two-dimensional crystal structure. [9]-[11] The band gap of $MoS_2$ can be modified either by reducing the number of layers [9,11-14] or by applying a large local uniaxial strain to the film/membrane [15]. The tunable band gap of the $MoS_2$ makes it promising for applications in optoelectronic devices, such as photodetectots,[16,17] photovoltaics, [18,] photocatalysts and light emitters [19].

An indirect to direct band gap transition from multilayer to monolayer results in pronounced enhancement in photoluminescence (PL) [,9,12] due to a very high quantum yield for monolayer $MoS_2$, which affirms the optical band gap at around 1.9 eV [9,10,12]. While bulk $MoS_2$ has a prominent direct band gap, PL in the bulk is nonexistent owing to excitonic absorption, yet when the direct band gap is dominant, for instance in monolayer regime, direct band radiative recombination becomes the principle method for exciton recombination. [12] It has been found that PL quantum yields for monolayer $MoS_2$ is about 3 orders greater than that of multilayer structure due to radiative recombination across the direct band gap. The PL quantum yield is greatly enhanced when the monolayer $MoS_2$ is suspended. [9] PL of $MoS_2$ is substantially affected by the nature of the substrate/interface, which may have effects on material performance. [20]

The atomically thin two-dimensional structure of $MoS_2$ films/membranes not only opens up new avenues in nanoelectronic and optoelectronic applications but also high surface-to-area ratios. These unique characters make few-layer $MoS_2$ flakes promising sensing devices to many adsorbates. In contrast to brittle bulk phase, mono- and few-layer $MoS_2$ flakes have superior elasticity and flexibility and hence are promising functional membranes. [21] For instance, a laminar separation membrane assembled from atomically thin $MoS_2$ sheets exhibits a water permeance which is 3-5 orders higher than that of graphene oxide membranes. [22]

Bertolazzi et. al recently measured elastic modulus and breaking strength of mono and bilayer $MoS_2$ membranes exfoliated from bulk and transferred onto an array of micro fabricated circular holes in a substrate. [23] According to their measurements, in-plane stiffness of monolayer $MoS_2$ is $180\pm60$ $Nm^{-1}$ and an effective Young's modulus of $270\pm100$ GPa, which is comparable to that of steel. These unique material properties of mono and multilayer $MoS_2$ sheets might make them suitable for a variety of applications such as reinforcing elements in composites and for fabrication of flexible electronic devices. For example, several groups recently developed flexible field-effect transistors (FETs) based on the large in-plane carrier mobility, robust mechanical properties, flexible and transparent nature, and low power dissipation of mono/few-layer $MoS_2$. [11,24,25] Further, monolayer $MoS_2$ has recently been utilized as a material for microelectromechanical systems (MEMS) and nanoelectromechanical systems (NEMS) devices. [1,9,11,26] Recently, a few research groups demonstrated the use of monolayer and multilayer $MoS_2$ in integrated circuits, although they were only in proof-of-concept stage. [27,28]

$MoS_2$ has recently garnered a lot of interest in biosensing applications due to its two-dimensional crystal structure, electronic properties, tunable band gap, high thermal and chemical stability. [29] Especially, $MoS_2$ has been utilized in electrochemical devices [30-32] and also in field-effect-transistor (FET) devices [33,34] to use as a biosensor for rapid and high-resolution biosensing applications. Ultrathin membranes are ideal candidates for base-resolution nanopore based DNA sequencing applications, because atomically thin membrane can amplify the baseline current and also the amplitude of the transient current drop without increasing the noise level, which results in a great enhancement in signal-to-noise SNR) ratio. In addition to the great enhancement in ionic current amplitude, transverse tunneling current can also be used for high-resolution electronic base detection. [35-37] This goal could be achieved using 2D materials like graphene [38-41] and transition metal dichalcogenides, for example $MoS_2$ [42,43] and boron nitride [44]. Several groups have recently shown high-resolution DNA detection using mono- and few-layer graphene nanopores [38-41], yet the large noise compared to traditional dielectric material based nanopores and the zero band gap property of graphene hinder the development of graphene-based nanopore sensors to achieve base-resolution detection. Even though a finite band gap can be engineered in pristine graphene, this increases the fabrication complexity and reduces the electronic mobility. The greater noise inherent with atomically thick single layer graphene can be reduced by using three-layer thick graphene (about 1 nm), which consequently increases the signal-to-noise ratio. In this perspective, atomically thin (about 0.8 nm) $MoS_2$ is a better alternative for graphene providing a better signal-to-noise ratio while maintaining its atomically thick property for base-resolution DNA detection. Another issue with graphene nanopores is that DNA sticks a lot to the pore wall as well as the surface during the translocation process due the strong π-π interaction between graphene and DNA, which could prove very challenging for nucleobase detection experiments via transverse tunneling current. In contrast, atomically thick $MoS_2$ can be engineered to have either Mo (molybdenum) or S (sulfur) or both Mo and S terminated sheets, which opens up a new avenue for base-resolution detection experiments.

Few-layer or even mono-layer $MoS_2$ flakes can be exfoliated from bulk crystalline material. Such flakes are widely used in research as they possess perfect crystalline structure as well as pristine quality. However, mechanical exfoliation is an extremely low yield process, which in general results in flakes a few micrometers to a few tens of micrometers in size. Therefore, the mechanical exfoliation approach is handicapped with respect to large-scale, high-quality flake fabrication. Chemical exfoliation is also another well-recognized exfoliation approach, which was known well before mechanical exfoliation. [45,46] There are two types of chemical exfoliation approaches, ion intercalation (the Morrison method) [45] and solvent-based exfoliation (the Coleman method) [47]. The Morrison method is handicapped by some major difficulties, such as relatively high temperature requirement (100° C.) and lengthy reaction time (three days), while the Coleman method suffers from low-yield of single-layer sheets and low $MoS_2$ flake concentration in solution. The chemical vapor deposition (CVD) method has gained great interest for fabricating mono- and few-layer $MoS_2$ sheets due to its ease of synthesis and high efficiency, together with its wide tolerance for growth parameters and substrates. [48-54]

In order to investigate the pristine material characterization of $MoS_2$ sheets, it is essential to have less-contaminated freestanding $MoS_2$ sheets over a freestanding window. Further, it is vital to synthesize high quality freestanding $MoS_2$ membranes for use in membrane-based applications such as nanopore devices, selective molecular sieving devices, gas sensors and other semiconductor devices. To date, production of freestanding $MoS_2$ requires transfer of $MoS_2$ sheets to an appropriately perforated substrate, which often introduces contaminants as well as unintentional wrinkles, cracks and tears into the sheets. In addition to the degradation of the quality of the $MoS_2$ sheets, the transfer process is extremely low-yield and is not scalable to a whole wafer such that there is sufficient amount of membrane surface area for use in membrane related experiments.

SUMMARY OF THE INVENTION

The invention provides novel methods for direct growth of freestanding membranes formed from two-dimensional (2D) materials, such as transition metal chalcogenides including molybdenum disulfide ($MoS_2$), across solid-state apertures; the materials formed using these methods have novel properties. The freestanding membranes are directly grown over an aperture by reacting two reactants, such as molybdenum trioxide ($MoO_3$) or molybdenum dioxide ($MoO_2$) and sulfur (S), in a chemical vapor deposition (CVD) process carried out at atmospheric pressure. Surprisingly, low-noise ultrathin membranes of the 2D material grow preferentially over apertures, resulting in intact pristine membranes that are one or a few layers thick. The mechanism by which this occurs is believed to be related to a thermal gradient that develops around the aperture, which favors aperture-limited growth.

According to the present invention, in situ fabrication of freestanding membranes onto a perforated substrate does not require transferring sheets of 2D material after its synthesis. As a consequence, the formed membrane retains its pristine quality with no contamination, resulting in ideal substrates for material characterization and membrane-based applications. Compared to prior methods of producing flakes of such materials and then transferring them to a suitable structure for device fabrication, the approach of the invention is more practical for obtaining large amounts of membrane with high yield.

One aspect of the invention is an ultrathin membrane containing a two-dimensional material. The membrane spans an aperture in a sheet of solid state material and is attached to a surface of the sheet in an area surrounding the aperture.

Another aspect of the invention is a method of fabricating an ultrathin membrane containing a two-dimensional material. The method includes the step of performing chemical vapor deposition of a first membrane precursor disposed on a first side of a sheet of solid state material including an aperture and a second membrane precursor disposed on a second side of the sheet, whereby the ultrathin membrane is formed from the first and second precursors across the aperture and contacts a surface of the sheet of solid state material in an area surrounding the aperture.

Still another aspect of the invention is a method of detecting a molecule. The method includes the steps of: (a) providing an ultrathin membrane as described above containing a nanopore, the membrane mounted in a device having electrolyte solution on both sides of the ultrathin membrane, an electrode in each electrolyte solution, and a device for measuring ionic currents through the nanopore; (b) measuring a baseline ionic current through the nanopore; and (c) observing blockage of the baseline ionic current by the molecule to detect the molecule, which is present in one of the electrolyte solutions.

The invention can be further summarized by the following list of items.

1. An ultrathin membrane comprising a two-dimensional material, the membrane spanning an aperture in a sheet of solid state material and attached to a surface of the sheet in an area surrounding the aperture.
2. The ultrathin membrane of item 1, wherein the two-dimensional material is selected from the group consisting of GaS, GaSe, InS, InSe, $HfS_2$, $HfSe_2$, $HfTe_2$, $MoS_2$, $MoSe_2$, $MoTe_2$, $NbS_2$, $NbSe_2$, $NbTe_2$, $NiS_2$, $NiSe_2$, $NiTe_2$, $PdS_2$, $PdSe_2$, $PdTe_2$, $PtS_2$, $PtSe_2$, $PtTe_2$, $ReS_2$, $ReSe_2$, $ReTe_2$, $TaS_2$, $TaSe_2$, $TaTe_2$, $TiS_2$, $TiSe_2$, $TiTe_2$, $WS_2$, $WSe_2$, $WTe_2$, $ZrS_2$, $ZrSe_2$, and $ZrTe_2$.
3. The ultrathin membrane of item 2, consisting essentially of $MoS_2$ or $MoSe_2$.
4. The ultrathin membrane of any of the preceding items, wherein the two-dimensional material is essentially monocrystalline.
5. The ultrathin membrane of any of the preceding items, wherein the membrane consists essentially of from one to several atomically thin sheets of the two-dimensional material.
6. The ultrathin membrane of any of the preceding items, wherein the thickness of the membrane is 1-2 atomic layers.
7. The ultrathin membrane of any of the preceding items, wherein the thickness of the membrane is from about 0.7 nm to about 10 nm.
8. The ultrathin membrane of any of the preceding items having a density of holes and atomic vacancies in the range from 0 to about 10 per $nm^2$.
9. The ultrathin membrane of any of the preceding items, which is essentially free of holes and atomic vacancies.
10. The ultrathin membrane of any of the preceding items having a specific conductance in the range from about 0.2 to about 1000 $nS/\mu m^2$.

11. The ultrathin membrane of any of the preceding items having a specific conductance of less than about 0.2 nS/μm².
12. The ultrathin membrane of any of the preceding items, wherein the aperture has a diameter from about 0.02 μm to about 2 μm.
13. The ultrathin membrane of any of the preceding items, wherein the membrane spans a plurality of apertures.
14. The ultrathin membrane of item 13, wherein the plurality of apertures is arranged in a two-dimensional array.
15. The ultrathin membrane of any of the preceding items, wherein the sheet of solid state material has a thickness in the range from about 5 nm to about 10 μm.
16. The ultrathin membrane of any of the preceding items, wherein the solid state material comprises a material selected from the group consisting of silicon nitride, silicon dioxide, hafnium oxide, titanium oxide, and aluminum oxide.
17. The ultrathin membrane of any of the preceding items, wherein the sheet of solid state material is mounted on a support structure.
18. The ultrathin membrane of item 17, wherein the support structure comprises silicon.
19. The ultrathin membrane of any of the preceding items, further comprising one or more nanopores, each nanopore having a diameter in the range from about 0.3 nm to about 50 nm.
20. The ultrathin membrane of item 19 having an ion current noise level of less than 400 pA at 200 kHz bandwidth.
21. The ultrathin membrane of any of the preceding items, wherein the membrane spans a plurality of apertures, and wherein the membrane comprises one or more nanopores within each aperture.
22. The ultrathin membrane of item 21, wherein the diameters of the nanopores are in the range from about 0.3 nm to about 50 nm.
23. The ultrathin membrane of item 21 configured for use as a water filter.
24. The ultrathin membrane of item 21 configured for use in biomolecule sequencing.
25. A method of fabricating the ultrathin membrane of any of the preceding items, the membrane comprising a two-dimensional material, the method comprising the step of performing chemical vapor deposition of a first membrane precursor disposed on a first side of a sheet of solid state material comprising an aperture and a second membrane precursor disposed on a second side of the sheet, whereby said ultrathin membrane is formed from the first and second precursors across the aperture and contacting a surface of the sheet of solid state material in an area surrounding the aperture.
26. The method of item 25, wherein the first membrane precursor comprises a metal selected from the group consisting of Ga, In, Hf, Mo, Nb, Ni, Pd, Pt, Re, Ta, Ti, W, and Zr.
27. The method of item 26, wherein the first membrane precursor is an oxide of said metal.
28. The method of any of items 25-27, wherein the second membrane precursor comprises S, Se, or Te.
29. The method of any of items 25-28, wherein the two-dimensional material formed is selected from the group consisting of GaS, GaSe, InS, InSe, $HfS_2$, $HfSe_2$, $HfTe_2$, $MoS_2$, $MoSe_2$, $MoTe_2$, $NbS_2$, $NbSe_2$, $NbTe_2$, $NiS_2$, $NiSe_2$, $NiTe_2$, $PdS_2$, $PdSe_2$, $PdTe_2$, $PtS_2$, $PtSe_2$, $PtTe_2$, $ReS_2$, $ReSe_2$, $ReTe_2$, $TaS_2$, $TaSe_2$, $TaTe_2$, $TiS_2$, $TiSe_2$, $TiTe_2$, $WS_2$, $WSe_2$, $WTe_2$, $ZrS_2$, $ZrSe_2$, and $ZrTe_2$.
30. The method of item 29, wherein the two-dimensional material consists essentially of $MoS_2$ or $MoSe_2$.
31. The method of any of items 25-30, wherein said chemical vapor deposition comprises heating the first membrane precursor and second membrane precursor in separate containers and in the presence of an inert carrier gas.
32. The method of item 31, wherein the container comprising the first membrane precursor is disposed near the first side of said sheet of solid state material, the container comprising the second membrane precursor is disposed remotely from said sheet of solid state material, and the heated second membrane precursor is carried towards the aperture by the carrier gas at the second side of said sheet of solid state material; and wherein the ultrathin membrane is fabricated on a surface of the sheet on the second side.
33. The method of item 27, wherein atoms of the second membrane precursor displace oxygen atoms of the oxide and form a two-dimensional material at the aperture.
34. The method of any of items 25-33, wherein the first and second membrane precursors are heated to about 650 to 800° C. at about 3 to 10° C./min under carrier gas flow, and held at about 650 to 800° C. for about 15 to 60 minutes.
35. The method of item 34 wherein, prior to said heating step, the first and second membrane precursors are heated to about 300 to 400° C. at a rate of about 20 to 30° C./min under carrier gas flow and held at about 300 to 400° C. for about 15 to 30 minutes.
36. The method of any of items 25-35, wherein said carrier gas flow is maintained at a rate of about 180 to 200 sccm.
37. The method of any of items 25-36, wherein said inert carrier gas is Ar or $N_2$.
38. The method of any of items 25-37, wherein the ultrathin membrane is fabricated across an aperture having a diameter of from about 0.02 μm to about 2.0 μm.
39. The method of any of items 25-38, wherein the solid state material is a material selected from the group consisting of silicon nitride, silicon dioxide, hafnium dioxide, titanium dioxide, and aluminum oxide.
40. The method of any of items 25-39, wherein the thickness of the ultrathin membrane is 1-2 atomic layers.
41. The method of any of items 25-40, wherein the ultrathin membrane is essentially free of holes and atomic vacancies.
42. The method of any of items 25-41, wherein the ultrathin membrane consists essentially of monocrystalline $MoS_2$ or $MoSe_2$.
43. The method of any of items 25-42, further comprising the step of forming one or more nanopores in the ultrathin membrane.
44. The method of item 43, wherein the one or more nanopores are formed using an electron beam, an ion beam, a laser, or application of voltage across the membrane.
45. The method of any of items 43-44, wherein the one or more nanopores each have a diameter in the range from about 0.3 nm to about 50 nm.
46. A method of detecting a molecule, the method comprising the steps of:
(a) providing the ultrathin membrane of item 19 mounted in a device having electrolyte solution on both sides of the ultrathin membrane, an electrode in each electrolyte solution, and a device for measuring ionic currents through a nanopore of the ultrathin membrane, wherein the electrolyte solution on one side of the ultrathin membrane comprises said molecule for detection;

(b) measuring a baseline ionic current through said nanopore; and (c) observing blockage of the baseline ionic current by said molecule.

47. The method of item 46, wherein the molecule is a nucleic acid or a protein.
48. The method of any of items 46-47, wherein the molecule is detected as it moves through the nanopore of said ultrathin membrane.
49. The method of any of items 46-48, wherein a nucleotide sequence or an amino acid sequence of the molecule is determined.
50. The method of item 48, wherein a protein is detected, and the protein reduces the ionic current through the nanopore for about 2 msec to about 5 msec.
51. The method of any of items 46-50, wherein the ultrathin membrane is functionalized in a region surrounding the nanopore with a functionalization moiety having a binding affinity for said molecule.
52. The method of item 51, wherein the functionalization moiety is an enzyme or an antibody.
53. The method of any of items 46-52, wherein at least one of said electrolyte solutions comprises an ionic species, the other of said electrolyte solutions comprises a fluorescent indicator that binds said ionic species and changes its fluorescence in response thereto, and a current through the nanopore carried by said ion is detected via the fluorescence of the indicator.
54. The method of item 53, wherein the ion is $Ca^{2+}$.
55. A device comprising at least one ultrathin membrane of any of items 1-24.
56. The device of item 55, wherein the ultrathin membrane comprises one or more nanopores.
57. The device of any of items 55-56 comprising at least 100 of said ultrathin membranes, each comprising one or more nanopores.
58. The device of any of items 55-57 configured to measure ionic conductance across the one or more nanopores individually.
59. The device of any of items 55-58 configured to optically measure ion fluxes through the one or more nanopores using a fluorescent indicator.
60. The device of any of items 55-59 configured to measure a vibration of the ultrathin membrane.
61. The device of any of items 55-60 configured as a sensor.
62. The device of item 56 configured as a filter.

BRIEF DESCRIPTION OF THE DRAWINGS

FIGS. 2A-2C show characterization by electron microscopy of $MoS_2$ membranes. FIG. 2A shows bright-field (BF) transmission electron microscopy (TEM) images of the CVD-assisted fabricated freestanding $MoS_2$ membranes over micron-scale holes fabricated in silicon nitride (SiN) sheets. Panels (i)-(iv) show BF-TEM images of four different $MoS_2$ membranes grown across micron-scale holes. The inset of a (i) shows the lithography assisted pattern written in the SiN sheet before $MoS_2$ growth by CVD. FIG. 2B shows high-resolution TEM (HRTEM) images of the freestanding $MoS_2$ membrane collected from the highlighted region in panel (i) shown with a dashed box. Panel (ii) shows single-layer and bilayer domains of $MoS_2$ in the SiN sheet across an approximately 6×6 $nm^2$ area. Panel (iii) shows an HRTEM image of a single-layer $MoS_2$ membrane corresponding to the domain highlighted in the dashed box in panel (ii). The upper inset shows the corresponding diffractogram of the monolayer. The bottom portion shows a line-profile scanned across 10 lattice points. The lattice constant of the (100) plane was 0.27 nm. Panel (iv) shows an HRTEM image of a bilayer $MoS_2$ domain from the area highlighted in the dashed box in panel (ii). The inset shows the corresponding diffractogram of bilayer $MoS_2$. FIG. 2C shows BF-TEM images of a different device with a five submicron hole pattern after $MoS_2$ growth, where four holes are completely covered with $MoS_2$ sheets. Panels (ii)-(iv) show BF-TEM images at different magnifications of one of the three holes as highlighted in the dashed box, which is completely covered with freestanding $MoS_2$ membrane. The different contrasts are due to the thickness variation of the $MoS_2$ membrane. The ripples in the $MoS_2$ membranes, which are due to strain applied on the SiN sheets, can clearly be seen in FIG. 2C (iii).

FIGS. 3A-3C show scanning transmission electron microscopy (STEM) images and secondary electron (SE) images of the device shown in FIG. 2A. FIG. 3A shows a STEM image of the same device shown in FIG. 2a, which confirms that $MoS_2$ grows on the trans side of the membrane (i.e., side that faces away from the $MoO_3$ boat). FIG. 3B shows a backscattering mode image of the same device, which further verifies that $MoS_2$ grows on the trans side of the membrane. FIG. 3C shows a high-resolution STEM image of a $MoS_2$ membrane collected in the highlighted region (dashed box) in FIG. 3A. The inset shows a diffraction pattern computed from the right side of the membrane, which corresponds to $MoS_2$ bilayer structure.

FIG. 6A shows a schematic representation of the device used for ion current measurements. FIG. 6B shows current-voltage curves of several nanopores (0.40 M KCl, pH 8, T=21° C., pore diameter d and conductance G indicated in legend). The current-voltage curve for d=0 is the horizontal line, and for d=16.3 nm is the line with greatest slope; the other lines have intermediate slopes proportional to the area of the nanopore. The inset shows a TEM image of several pores drilled adjacent to each other (scale bar=5 nm). FIG. 6C shows a comparison of experimental G and d values with theoretical curves computed for 1 to 4 MoS$_2$ layers.

FIG. 8A shows a three-second continuous current trace for a 2.3 nm diameter pore after the addition of 20 nM of 153-mer ssDNA to the cis chamber ([KCl]=0.40 M, $V_{trans}$=200 mV, sampling rate=4.17 MHz, data low-pass filtered to 200 kHz). Concatenated sets of events at different magnifications are shown below the trace. FIG. 8B shows a scatter plot of fractional current blockade vs. dwell time $t_d$, as well as histograms of each parameter shown on each corresponding axis (n=number of molecules detected).

DETAILED DESCRIPTION OF THE INVENTION

The invention provides freestanding ultrathin membranes of two-dimensional (2D) materials having unique properties including a pristine, monocrystalline or polycrystalline morphology that is robust and essentially free of defects, and provides exceptionally low electrical noise when measuring ionic currents through nanopores for biomolecule sequencing applications. The membranes are fabricated by a novel chemical vapor deposition process that produces aperture-dependent growth of a variety of 2D materials and avoids the need to transfer flakes of such materials to an aperture for various applications, with consequent introduction of structural defects and contamination. The fabrication process can provide membranes of large surface area, rendering them useful for water filtration applications. The membranes of the present invention also can be used as components of electronic devices, such as FETs or components of MEMS or NEMS devices.

Figure 1A:
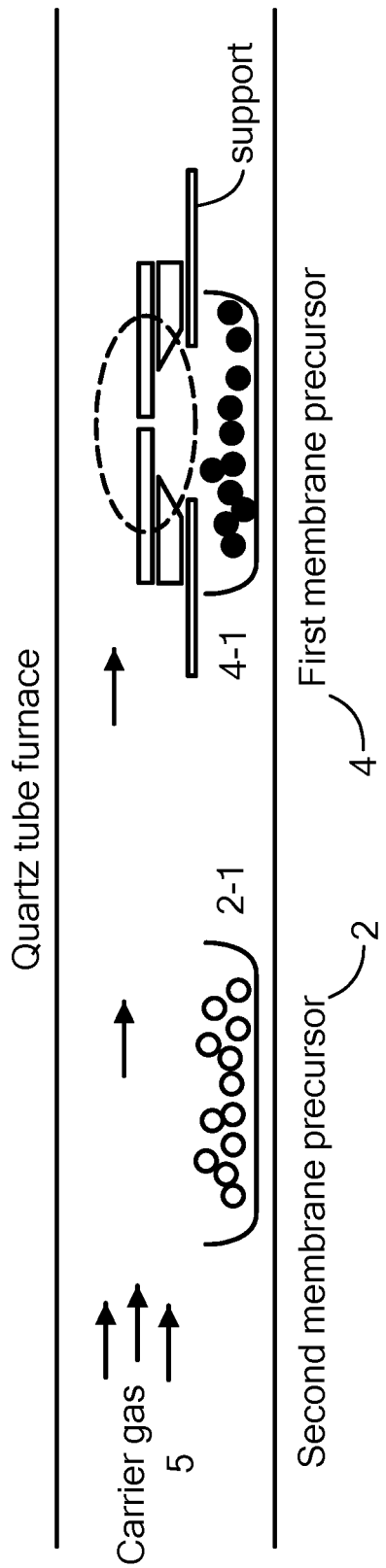
FIG. 1A shows a schematic illustration of an aperture-limited freestanding ultrathin membrane fabrication process. A sheet of solid state material that contains a micron-scale hole (or array of holes) is placed over a boat containing a first membrane precursor in a quartz furnace. After an initial sublimation of the first membrane precursor material, temperature and carrier gas flow are adjusted such that a sublimated second membrane precursor material flows over the aperture.
Figure 1B:
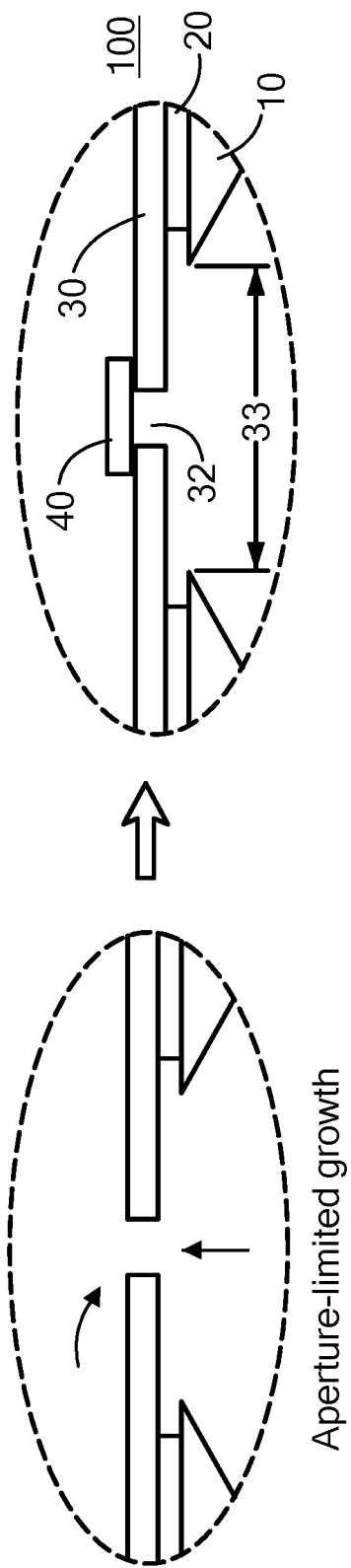
FIG. 1B shows a schematic illustration of a proposed mechanism by which aperture-limited growth of membrane occurs. Elements in the figure are not to scale.

An exemplary fabrication method is summarized by the fabrication scheme shown in FIGS. 1A and 1B. First, substrate or support structure 10 (e.g., silicon chips, optionally coated with a layer of silicon oxide 20) having window 33, over which is deposited a thin freestanding sheet 30 of a solid state material (e.g., 30-50 µm$^2$ of SiN of 100 nm thickness), is hot piranha cleaned and dried with a gentle flow of nitrogen (N$_2$) gas, followed by warm deionized (DI) water rinsing. Next, positive electron beam resist is spun onto the cleaned and dried chip, and then one or more micron-scale apertures (optionally an array of such apertures) are written on the freestanding SiN membrane using e-beam lithography and subsequently developed. Then, SiN is controllably etched through the apertures in SiN membrane using an SF$_6$ reactive ion etch (RIE) plasma to produce one or more corresponding apertures 32 in the SiN sheet. Subsequently, the resist is stripped off using an acetone bath and hot piranha treatment. A freestanding membrane of 2D material, such as MoS$_2$, then can be grown directly onto the aperture or pre-patterned array of apertures in the SiN sheet to form membrane device 100. For example, the membrane can be grown using molybdenum trioxide (MoO$_3$) and sulfur (S) as precursors in a chemical vapor deposition (CVD) process carried out at 750-800° C. and atmospheric pressure. In such a CVD process, first membrane precursor 4 (e.g., MoO$_3$ powder) is placed into boat 4-1 or other container in the CVD furnace, and second membrane precursor 2 (e.g., sulfur powder) is placed into boat 2-1 or other container in the CVD furnace.

The placement of the membrane precursor materials in the furnace is important. The prepared freestanding solid state sheet with its supporting substrate is placed above the first membrane precursor container such that sublimating first membrane precursor can rise up and contact the aperture in the solid state sheet where membrane fabrication is desired. The second membrane precursor container is placed upstream of the first membrane precursor container with respect to the flow of inert carrier gas 5, such that sublimating second membrane precursor rises up and is carried toward the aperture for membrane formation by the carrier gas. The flow of carrier gas is arranged so that the second membrane precursor is delivered by the carrier gas to the opposite side of the aperture from the side contacted by sublimating first membrane precursor. The membrane is formed on the side of the aperture to which the second membrane precursor is delivered; that side is referred to as the "trans" side of the device, the other side being the "cis" side.

Figure 1C:
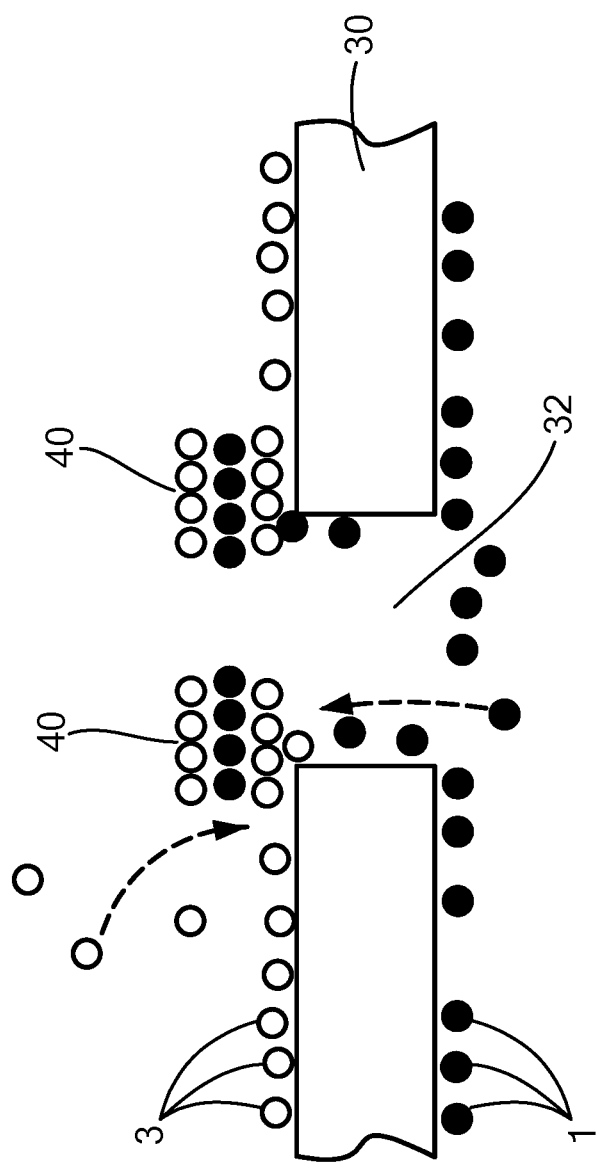
FIG. 1C shows further detail of the proposed mechanism.

FIG. 1C presents a model of the mechanism of membrane formation. Transition metal atoms 1 from the first membrane precursor accumulate on the underside (i.e., the cis side) of the sheet of solid state material 30 and inside of aperture 32. Atoms 3 of second membrane precursor accumulate on the upper side (i.e., the trans side) of the sheet. Both sets of atoms react and build membrane 40 at the trans side. The membrane structures depicted in FIG. 1C are nucleation structures which grow from the perimeter inwards toward the center to complete the membrane. While membrane formation is aperture limited, i.e., it occurs preferentially at apertures in the solid state sheet material, the finished membrane not only covers the aperture completely but also covers the trans side solid state sheet in a region surrounding the aperture, forming a leak-proof seal. If membrane growth is allowed to continue, membrane formation can continue at the trans side of the sheet and fuse to form a continuous sheet of membrane covering the sheet.

Figure 1D:
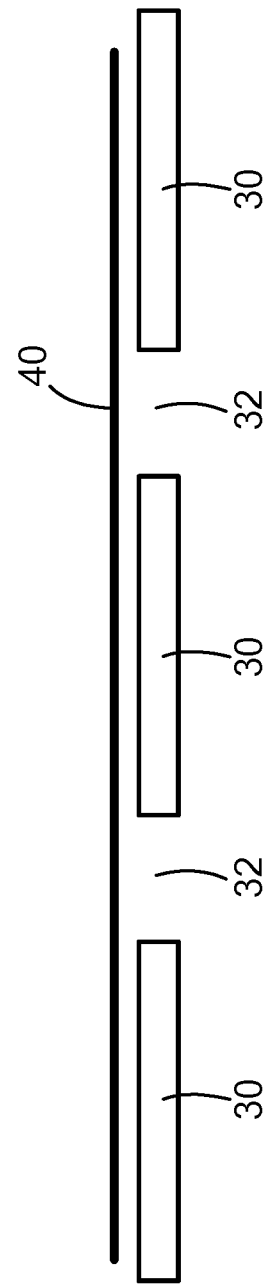
FIG. 1D shows a schematic illustration of a portion of a filter device of the invention.

When the membrane fabrication process is allowed to form a continuous sheet of membrane, e.g., covering a plurality of apertures or an array of apertures, the resulting structure can form a filter device, a portion of which is depicted in FIG. 1D. In such a device, solid state sheet 30 containing apertures 32 is covered by a continuous sheet of 2D membrane 40, which provides a sieving effect, for example, allowing water molecules to penetrate but holding back dissolved solutes. Optionally, one or more nanopores can be introduced into the membrane at each aperture to provide pathways for desired solutes to pass through the filter, depending on their size or other molecular properties. In addition, the membrane and/or nanopores can be functionalized or chemically modified in order to confer selectivity to the molecular sieving effect of the filter.

The membrane can have a polycrystalline or monocrystalline structure and is preferably atomically thin, i.e., containing 1, 2, 3, 4, 5, 6, 7, 8, 9, or 10 layers of 2D material. Preferably, the membrane has a thickness in the range from about 0.7 nm to about 10 nm. For example, the membrane thickness can be less than 10, 9, 8, 7, 6, 5, 4, 3, 2, or 1 nm. In preferred embodiments, the membrane has 1 or 2 layers (i.e., 1-2 atomic layers) of 2D material, or a mixture of regions having 1 and regions having 2 layers. For example, a $MoS_2$ membrane having 1 atomic layer refers to a 2D monocrystalline or polycrystalline arrangement having a single layer of $MoS_2$ molecules, and it is understood that such a single layer may have sublayers of Mo and S atoms as dictated by the crystal structure. In certain preferred embodiments, the membrane is free of holes, atomic vacancies, or other structural defects over the entire area of membrane covering the aperture. In other preferred embodiments, the membrane contains 10 or fewer, 9 or fewer, 8 or fewer, 7 or fewer, 6 or fewer, 5 or fewer, 4 or fewer, 3 or fewer, 2 or fewer, or 1 or fewer holes or atomic vacancies per $nm^2$ of membrane area covering the aperture. The density of holes or atomic vacancies can be controlled during fabrication in order to produce desired properties, such as desired molecular size cutoff in filtration.

A variety of 2D materials, i.e., materials that form atomically thin monocrystalline or polycrystalline two dimensional sheets, can be used to form the membrane. Such materials include GaS, GaSe, InS, InSe, $HfS_2$, $HfSe_2$, $HfTe_2$, $MoS_2$, $MoSe_2$, $MoTe_2$, $NbS_2$, $NbSe_2$, $NbTe_2$, $NiS_2$, $NiSe_2$, $NiTe_2$, $PdS_2$, $PdSe_2$, $PdTe_2$, $PtS_2$, $PtSe_2$, $PtTe_2$, $ReS_2$, $ReSe_2$, $ReTe_2$, $TaS_2$, $TaSe_2$, $TaTe_2$, $TiS_2$, $TiSe_2$, $TiTe_2$, $WS_2$, $WSe_2$, $WTe_2$, $ZrS_2$, $ZrSe_2$, and $ZrTe_2$. The 2D materials can be, for example, transition metal chalcogenides or semimetal chalcogenides. Preferred 2D materials for the membrane are $MoS_2$ and $MoSe_2$. Suitable membrane materials can be fabricated in an aperture-limited fashion by CVD from two or more membrane precursor materials. The membrane precursor materials can be any chemical precursor of the membrane material compatible with the conditions required for CVD, and which react under the conditions of CVD to produce the membrane material in an aperture-limited fashion. Required properties of the precursor materials include thermal stability to several hundred degrees C. and ability to sublimate at such temperatures and bind the solid state sheet at the aperture.

In some embodiments, the device contains a substrate or support structure attached to the sheet of solid state material that carries the membrane. The support structure contains a window that provides access of fluid to the membrane. In some embodiments, the device contains an insulating layer disposed between the support structure and the sheet of solid state material. The supporting structure can comprise or consist of silicon, silicon dioxide, glass, quartz, or mica. In preferred embodiments, the support structure is silicon. The insulating layer can comprise or consist of silicon dioxide, glass, quartz, or mica. In preferred embodiments, the support structure is silicon, coated in whole or in part by an insulating layer of silicon dioxide. In some embodiments, the support structure and the insulating layer, if present, contain a plurality of windows, each window providing access to at least one well. In some embodiments the support structures contain one or more scored lines between two or more windows, the scored lines enabling the division of the device into two or more pieces, each piece containing one or more windows. In some embodiments, the device has at least 5, at least 10, at least 20, at least 50, at least 100, at least 150, or at least 200 windows.

The sheet of solid state material comprises or consists of silicon nitride, silicon dioxide, aluminum oxide, titanium oxide, or hafnium oxide. The sheet has a thickness in the range from about 5 nm to about 10 µm. In preferred embodiments, the substrate is about 100 nm thick. The sheet of solid state material contains one or more apertures covered by membrane of 2D material. The apertures are generally circular, but could have another shape. The apertures have a diameter, or largest dimension across, in the range from about 0.02 µm to about 2 µm. In some embodiments, each aperture has a diameter of less than 2 µm, less than 1.5 µm, less than 1.2 µm, less than 1 µm, less than 750 nm, less than 500 nm, less than 400 nm, less than 300 nm, less than 200 nm, or less than 100 nm.

Figure 6A:
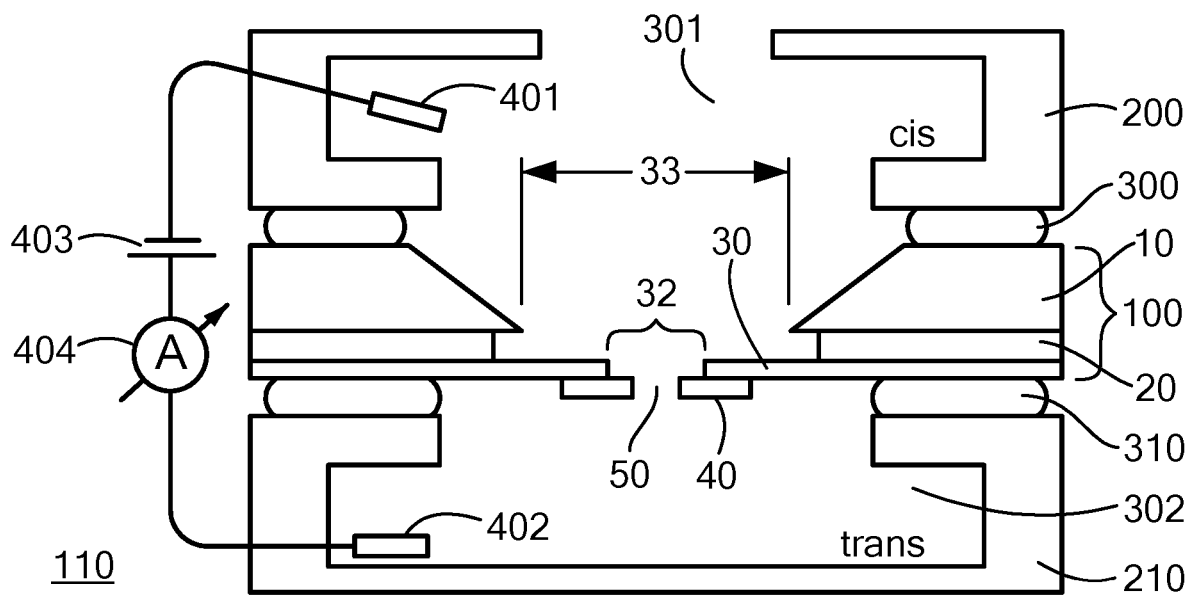
FIGS. 6A-6C show ion transport measurements through nanopores in $MoS_2$ membrane devices.

The invention includes an apparatus for the study of polymers, such as biopolymers, including polynucleotides, polypeptides, peptides, proteins, oligosaccharides, and polysaccharides, as they are transported through nanopores in a 2D material membrane. An embodiment of such an apparatus is depicted in FIG. 6A. Apparatus 110 includes nanopore membrane device 100, wherein membrane 40, containing nanopore 50, is positioned between first fluid reservoir 301 and second fluid reservoir 302; an electrode pair having first electrode 401 disposed in the first fluid reservoir and second electrode 402 disposed in the second fluid reservoir; voltage source 403 for establishing a voltage between the electrodes; and circuit 404 capable of detecting an electrical signal (e.g., ionic current through the nanopore) that correlates with the sequence of the polymer, or another aspect of the polymer molecule. The membrane device can be attached via adhesive layers 300 and 310 to first and second chambers (200 and 210 respectively), which can be constructed, for example, of a chemically inert polymer material such as PTFE, or of silicon, silicon dioxide, or quartz.

The membranes of the present invention are essentially free of structural defects. Defects such as cracks, holes, and atomic vacancies may allow ions or other solutes to pass through the membrane, thereby interfering with uses of the membrane including measuring ionic current to characterize polymers, and filtration. The presence of an intact membrane can be inferred from low specific conductance of the membrane. For example, while testing using a 1M or 0.4M solution of KCl at room temperature, the specific conductance may be less than 0.1 $nS/\mu m^2$, less than 0.2 $nS/\mu m^2$, less than 0.3 $nS/\mu m^2$, less than 0.5 $nS/\mu m^2$, less than 0.7 $nS/\mu m^2$, less than 1 $nS/\mu m^2$, less than 1.5 $nS/\mu m^2$, less than 2 $nS/\mu m^2$, less than 5 $nS/\mu m^2$, less than 10 $nS/\mu m^2$, or less than 20 $nS/\mu m^2$. Higher values of conductance can be useful in certain applications, such as selective filtration designed to trap only specific solutes or classes of solutes. Generally, the specific conductance is in the range from about 0.2 $nS/\mu m^2$ to about 1000 $nS/\mu m^2$. In a preferred embodiment, the specific conductance is less than 0.2 $nS/\mu m^2$ when measured using 0.4M KCl. With membranes of the present invention, the background electrical noise from the membrane itself, e.g., when measuring ionic currents through a nanopore in the membrane, is preferably less than 400 pA at 200 kHz bandwidth (i.e., low-pass filtered at 200 kHz).

Because the fabrication method of the present invention avoids transfer of the membrane after fabrication, the method reliably produces intact membranes that are free of cracks. For example, the percentage of intact membranes produced by the method may be greater than 60%, greater than 70%, greater than 80%, greater than 85%, greater than 90%, greater than 95%, greater than 98%, or greater than 99%. Whether a membrane is intact may be determined, for example, from its ionic conductance. Thus, a membrane may considered intact if the ionic conductance across the membrane is less than 0.1 nS/$\mu m^2$, less than 0.3 nS/$\mu m^2$, less than 0.5 nS/$\mu m^2$, less than 0.7 nS/$\mu m^2$, less than 1 nS/$\mu m^2$, less than 1.5 nS/$\mu m^2$, less than 2 nS/$\mu m^2$, less than 5 nS/$\mu m^2$, less than 10 nS/$\mu m^2$, or less than 20 nS/$\mu m^2$. The percentage of intact membranes also can be determined by inspection using electron microscopy.

For certain uses, one or more nanopores may be created in the membrane. As used herein, a "nanopore" is a pore having a diameter from about 0.3 nm to about 999 nm. However, in preferred embodiments, nanopores from about 0.3 to about 50 nm are used. The number of nanopores created per membrane may vary depending on the intended application of the membrane. For example, membranes designed for use in determining the sequence of bases in a polynucleotide may have only a single nanopore per membrane. Alternatively, membranes designed for use in deionization of aqueous solutions may have a plurality of nanopores per membrane.

EXAMPLES

Example 1. Fabrication of Freestanding Ultrathin MoS$_2$ Membranes

Substrates for nanopore fabrication were 5 mm×5 mm square Si chips with a 100-nm-thick SiN film deposited on a 2.5 μm thick thermal SiO$_2$ layer. The oxide layer helps to reduce electrical noise. The SiN film was protected with a 950 PMMA etch mask, and a small (2 μm×2 μm) region with a pattern of four 600 nm-diameter holes and a central 1.5 μm diameter hole was exposed using Nabity NPGS e-beam writing software on a Hitachi S-4800 scanning electron microscope. Exposed PMMA was developed with 3:1 isopropyl alcohol and methyl isobutylketone. The SiN film was etched to AFM- and ellipsometry-calibrated thickness in a Technics Micro-RIE Series 800 etcher using sulfur hexafluoride (SF$_6$) at 300 mTorr and 150 W. PMMA was removed using acetone, and chips were cleaned with hot piranha solution followed by warm water to remove residual PMMA.

MoS$_2$ membranes were synthesized using an atmospheric-pressure CVD process in a split tube furnace with a 35 mm O.D. quartz tube as follows. The chips were placed in the center of the furnace, suspended about 3 mm above MoO$_3$ powder, and sulfur powder was placed in the upstream region of the furnace chamber.

Ar gas was flowed at 200 sccm through the chamber throughout the growth process as well as during the cooling process. First the temperature of the furnace was ramped from room temperature up to 300° C. at a rate of 30° C./min and held at the target temperature (300° C.) for 15 min to allow for sufficient MoO$_3$ sublimation. Next, the temperature of the furnace was raised to 750° C. at a rate of 3° C./min, and sulfurization was allowed to proceed for 90 minutes. After that, the furnace was cooled down to room temperature under the continued flow of Ar gas, through the complete opening of the hood of the furnace.

Example 2. Structural Characterization of MoS$_2$ Membranes

FIG. 2A shows bright-field (BF) TEM images of freestanding MoS$_2$ membranes synthesized, without a substrate, onto micron-scale holes prefabricated in a thin sheet of SiN. Panels (i)-(iv) of FIG. 2A show high magnification TEM images of four different MoS$_2$ membrane devices. Some holes are partially covered with multiple layers of MoS$_2$, which possibly could be due to the insufficient nucleation time during CVD. It is noteworthy that unintentional wrinkles could be seen in some MoS$_2$ membranes grown across holes, which may be due to stress exerted on the membranes as they freely suspend over the free aperture (see, e.g., FIG. 2A(iii)). Different domains of monolayer and multilayer MoS$_2$ were observed in membranes grown across submicron aperture regions.

FIG. 2B shows high resolution TEM (HRTEM) images of the MoS$_2$ membrane analyzed in the highlighted region as depicted in FIG. 2A(i) with a dashed box. In FIG. 2B it is clear that there were still some incompletely nucleated sites, as highlighted in FIG. 2B(iii) with a dashed box. In FIG. 2B(ii), monolayer and bilayer domains of MoS$_2$ can clearly be seen in the freestanding membrane across an area of approximately 6 nm×6 nm. Partially nucleated or incompletely nucleated sites can also be observed in FIG. 2B(ii). FIG. 2B(iii) shows an HRTEM image of single layer MoS$_2$ membrane corresponding to the domain highlighted in the dashed box in panel (ii). The upper inset shows the corresponding diffractogram of the image, which further verifies the existence of monolayer MoS$_2$ in the region highlighted with the dashed box in FIG. 2B(ii). The line-profile was manipulated by scanning across 10 lattice points (as depicted in FIG. 2B(iii)), which gave a lattice constant of MoS$_2$ in the (100) plane of 0.27 nm (bottom inset). FIG. 2B(iv) shows an HRTEM image of a bilayer MoS$_2$ domain corresponding to the area highlighted in the dashed box in FIG. 2B(ii). The two hexagonal lattice structures next to each other corresponding to two layers of MoS$_2$ can be seen vividly in FIG. 2B(iv). The inset illustrates the corresponding diffractogram of bilayer MoS$_2$ membrane.

FIG. 2C shows BF-TEM images of a device with a five submicron hole pattern after MoS$_2$ growth, where four holes are completely covered with MoS$_2$ membranes. The inset of FIG. 2C(i) shows the perforated substrate with an e-beam written five-hole pattern before MoS$_2$ growth. Panels (ii)-(iv) of FIG. 2C show BF-TEM images of one of the membranes highlighted in FIG. 2C(i) with a dashed box. These CVD-grown freestanding MoS$_2$ membranes contain different numbers of layers localized on the membrane as seen in FIG. 2C(ii). Unintentionally generated wrinkles in the MoS$_2$ membranes can be seen in FIG. 2C(iii), which is likely due to strain applied to the freestanding MoS$_2$ membranes across the free aperture. It is noteworthy that there was a preference of growing MoS$_2$ membranes across cracks that were generated during the e-beam writing process and subsequently developed in CVD temperature ramping (not shown).

FIG. 3A shows an STEM image of the same sample shown in FIG. 2A(i). According to FIG. 3A, MoS$_2$ membrane was grown 100% of the time in the crater side of the membrane. FIG. 3B illustrates the same membrane imaged in the backscattering mode (SE mode) from the crater side, which further verifies that MoS$_2$ membrane was completely been grown on the crater side, and that the "top" of the sample is the membrane side on which there is no MoS$_2$. This is an interesting observation, because the chip was placed facing membrane side down during CVD operation, whereby the chip was suspended about 3 mm above the MoO$_3$ powder. Therefore having MoS$_2$ completely grown on the crater side (and not on the membrane or top side) explains the growth mechanism of MoS$_2$ across a perforated substrate. One possible explanation is that sublimated MoO$_3$ leaks through the apertures in the SiN membrane and precipitates onto the crater side of the membrane due to the temperature gradient between top and bottom sides of the chip. Sulfurization takes place with the flow of sublimated S placed in the upstream portion of the chamber, which results in fabricating MoS$_2$ sheets across the apertures in the substrate. This proposed mechanism is further verified from FIG. 2D, panels (i)-(iv), where there is a higher affinity in growing MoS$_2$ sheets across sub micrometer slits in SiN freestanding window. FIG. 3C shows a high-resolution STEM image of one of the freestanding MoS$_2$ membranes highlighted in FIG. 3A with a dashed box, which clearly demonstrates some Moiré patterns. The FFT collected in the vicinity of the Moiré patterns (inset, FIG. 3C) confirms that it is bilayer MoS$_2$, where two sheets are slightly rotated on top of each other.

Figure 4A:
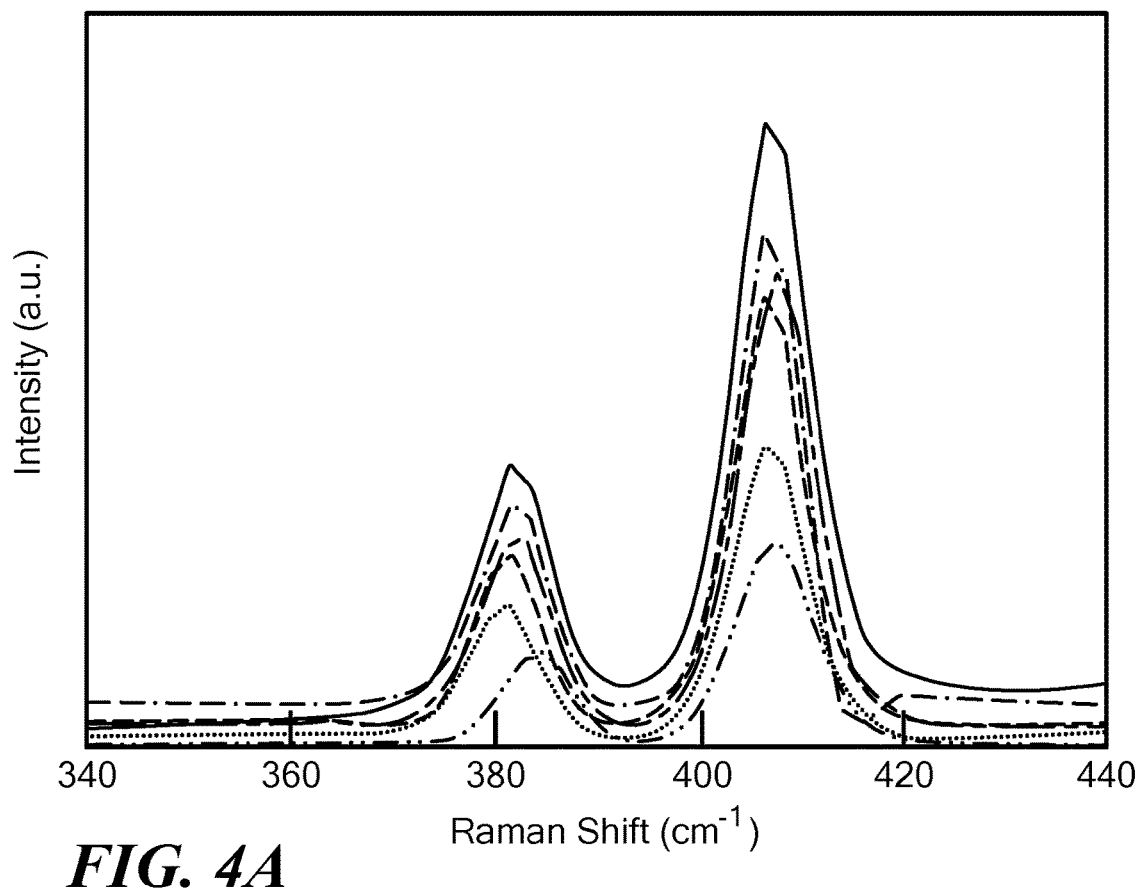
FIG. 4A shows Raman characterization of $MoS_2$ membranes. The Raman spectra were collected in the vicinity of the center hole in the device shown in FIG. 2A, which corresponds to $MoS_2$ sheets that are 2-3 layers thick.

Raman spectroscopy measurements were carried out in the vicinity of the middle hole in the five-hole pattern (highlighted with dashed box in FIG. 2A) to probe the thickness as well as the crystal quality of the as-grown freestanding MoS$_2$ membranes (FIG. 4). Raman spectroscopy was carried out using a Jobin Yvon LabRam HR800 spectrometer attached to an Olympus BH2 microscope. MoS$_2$ AND MoSe$_2$ membranes were imaged using a JEOL 2010FEG transmission electron microscope operating in bright-field mode at 200 kV, and STEM images were collected using a Hitachi HD 2700 at 200 kV, Cs-corrected. Two major Raman features are prominent in the resulting Raman spectrum in FIG. 3A: E2g1 (383 cm$^{-1}$), which corresponds to an in-plane mode resulting from the opposite vibration of two S atoms with respect to the Mo between them, and A1g (406 cm$^{-1}$), which is attributed to the out-of-plane vibration of only S atoms in opposite directions. [55-57] The frequency-shift difference between E2g1 and A1g modes is correlated to the number of layers in the multilayer MoS$_2$ membranes. [58] According to the frequency-shift difference (about 23 cm$^{-1}$) between the two modes, the center hole (about 2 μm) was mostly covered with the 2-3 layer thick MoS$_2$ membranes.

Example 3. Electrical Characterization of MoS$_2$ Membranes Containing Nanopores Following optimization of hole-free membrane growth, complete MoS$_2$ membranes were grown on several devices, and a TEM beam was used to fabricate nanopores in these membranes in order to study ion transport through the pores. Because of the extremely thin membrane structure, only brief (about 1-2 sec) exposure times using a focused beam were sufficient to produce nanopores; great care was taken to avoid large pore formation, e.g., by reduction of spot size and beam current.

Figure 6B:
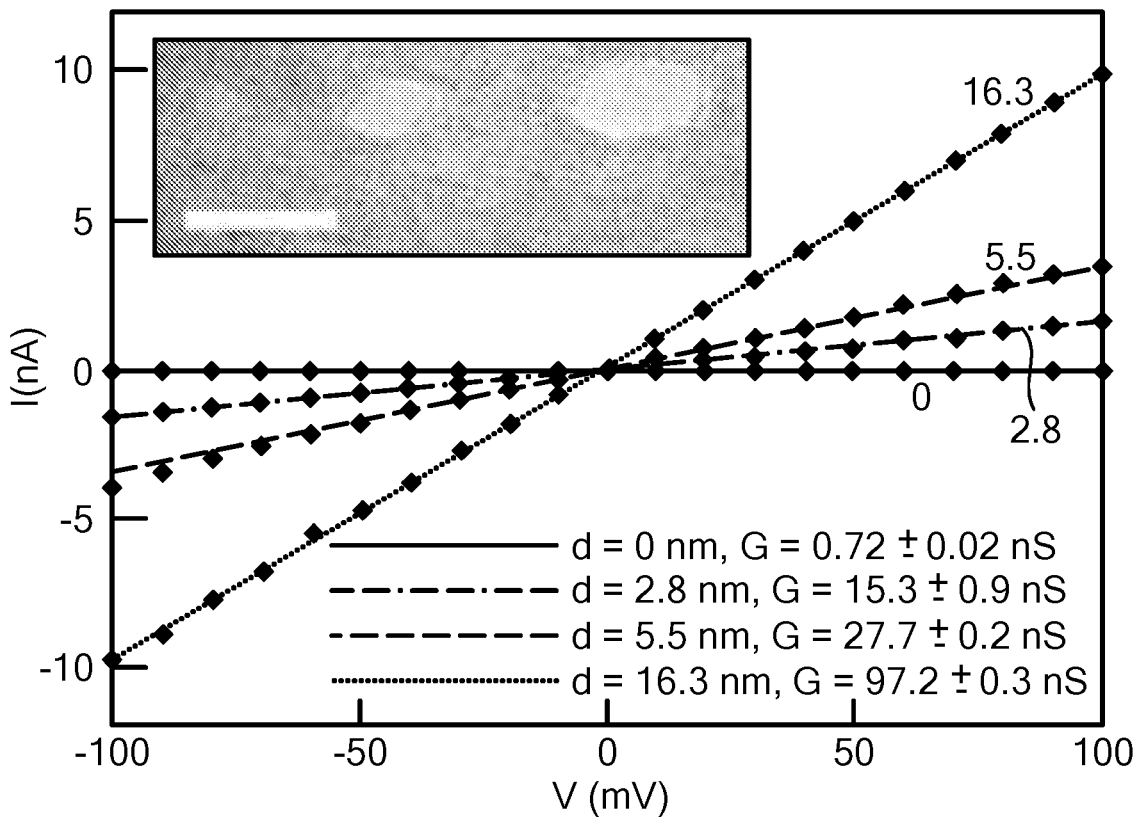

Following the fabrication of several pores of different diameters, the chips were assembled into a custom-made PTFE cell as shown in FIG. 6A. Prior to obtaining measurements, a chip was glued onto the top PTFE portion of the cell using a quick-curing elastomer, and a second layer of glue was applied to the membrane such that only about 1 mm$^2$ was exposed, in order to minimize capacitance-mediated noise. After elastomer curing, the cell was assembled, the cis and trans compartments were filled with 0.40 M KCl electrolyte buffered to pH 8.0 using 10 mM Tris ($G_{bulk}$=50 mS/cm), and a pair of Ag/AgCl wire electrodes was immersed in the chambers. The electrodes were connected to a Chimera Instruments high-bandwidth amplifier. FIG. 6B shows the current-voltage response of the MoS$_2$ membranes with pores of various diameters. While no appreciable current was measured for the membrane without pores linear current/voltage responses were observed for the three nanopores tested. The responses were characteristic of ion-conducting nanopores. Linear fitting of the slopes of the curves yielded the membrane conductance (G) values which are reported in the legend of FIG. 6B. The inset TEM image (JEOL 2010FEG operating in bright-field mode at 200 kV) shows several nanopores fabricated adjacent to one another using an electron beam, ranging in diameter from 1 to 5 nm.

Figure 6C:
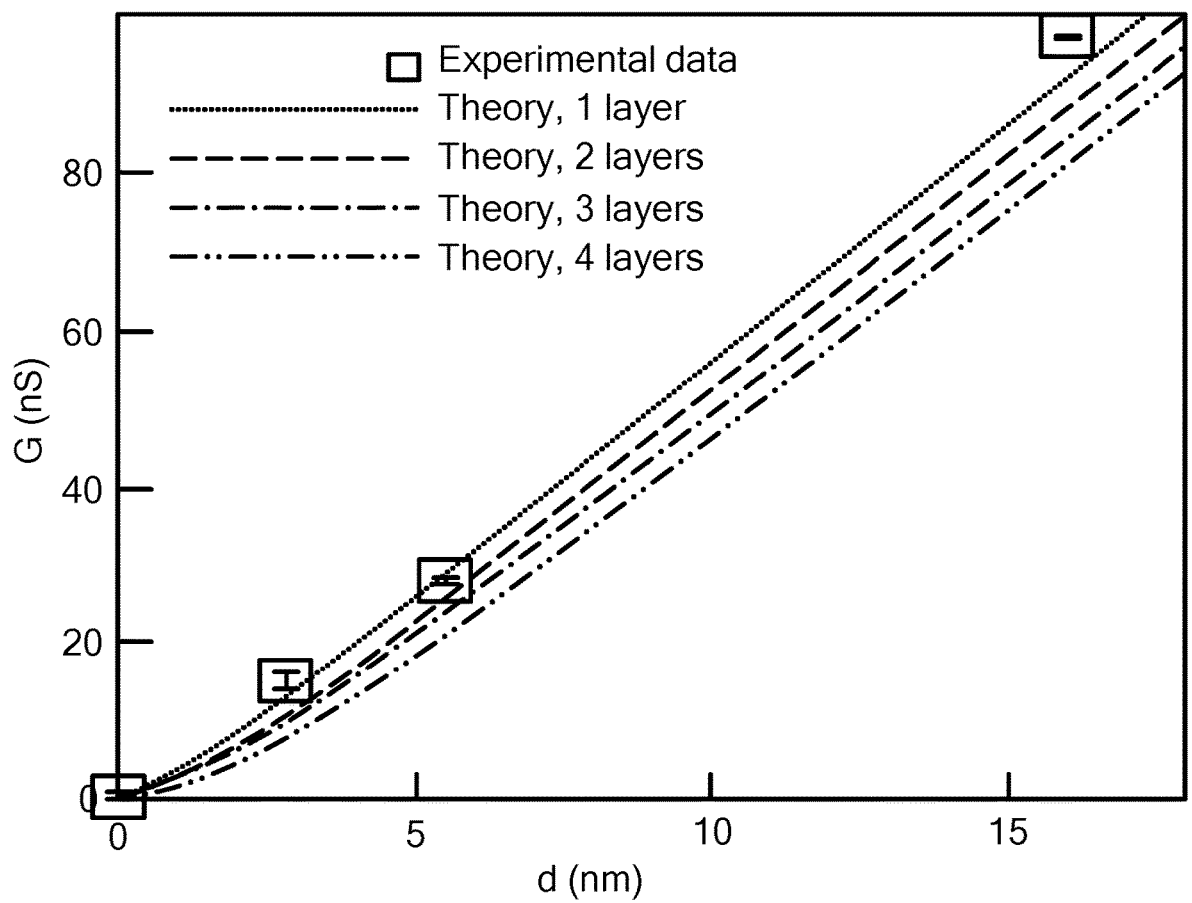

To rationalize the observed conductance levels to these pore diameters, the theoretically expected conductance values for circular nanopores of ideal diameter d are plotted in FIG. 6C. The values for MoS$_2$ membranes of quantized thicknesses in the range of 1-4 layers (where each layer is 0.8 nm thick), are also shown in FIG. 6C. To obtain these curves, the access resistance in ultrathin membranes was taken into account, yielding the conductivity G for a MoS$_2$ membrane containing a pore of diameter d as described in Equation (1)

$$G(d)=\sigma(4nh/\pi d^2+1/d)^{-1} \qquad (1)$$

where σ is the bulk electrolyte conductivity, n is the number of MoS$_2$ layers, and h is the thickness of a monolayer (0.8 nm). In FIG. 6C the conductance for three MoS$_2$ membranes that contained no fabricated nanopores are also plotted, in which the mean conductance was 0.43 nS, a factor of 35 smaller than the conductance of the 2.8 nm pore. Overall, the experimental data indicated pores that of 1-2 layers thickness, apart from a small negative deviation for the larger pore, which most likely stems from about 10% error in pore diameter.

Figure 7A:
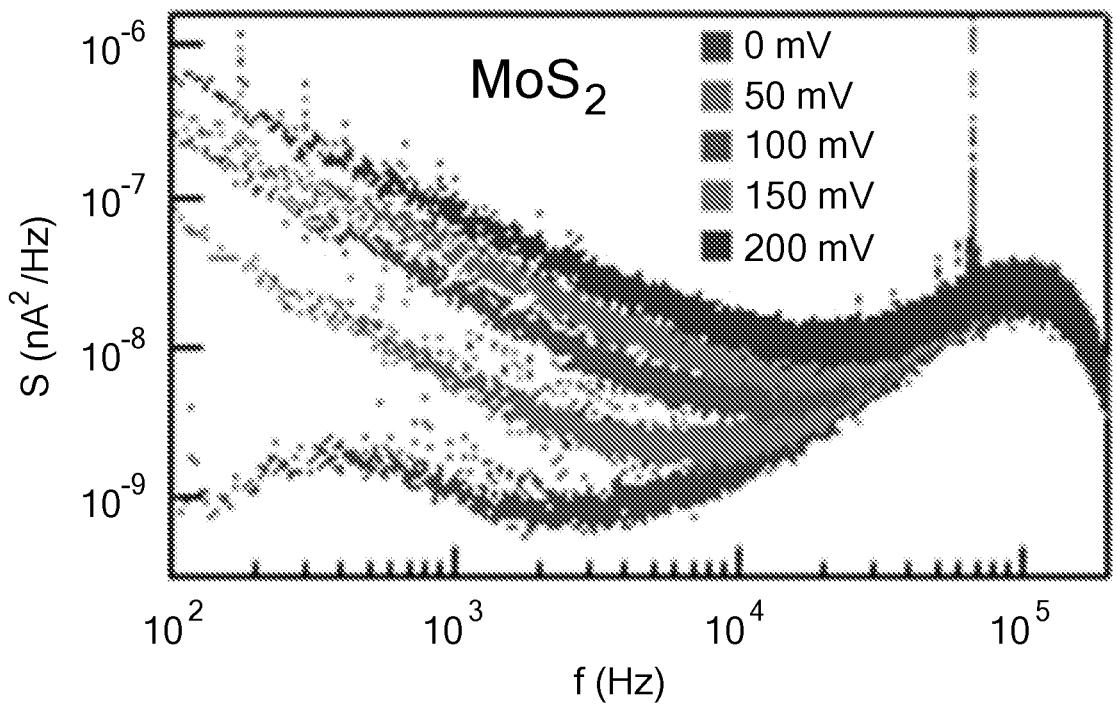
FIG. 7A shows ion current noise power spectral densities (PSD) for a MoS$_2$ membrane containing a 2.8 nm diameter pore at different applied voltages (the applied voltages range from 0 (bottom) to 200 mV (top) at the left side of the figure). The solution was 0.40M KCl, pH 8, T=21° C.
Figure 7B:
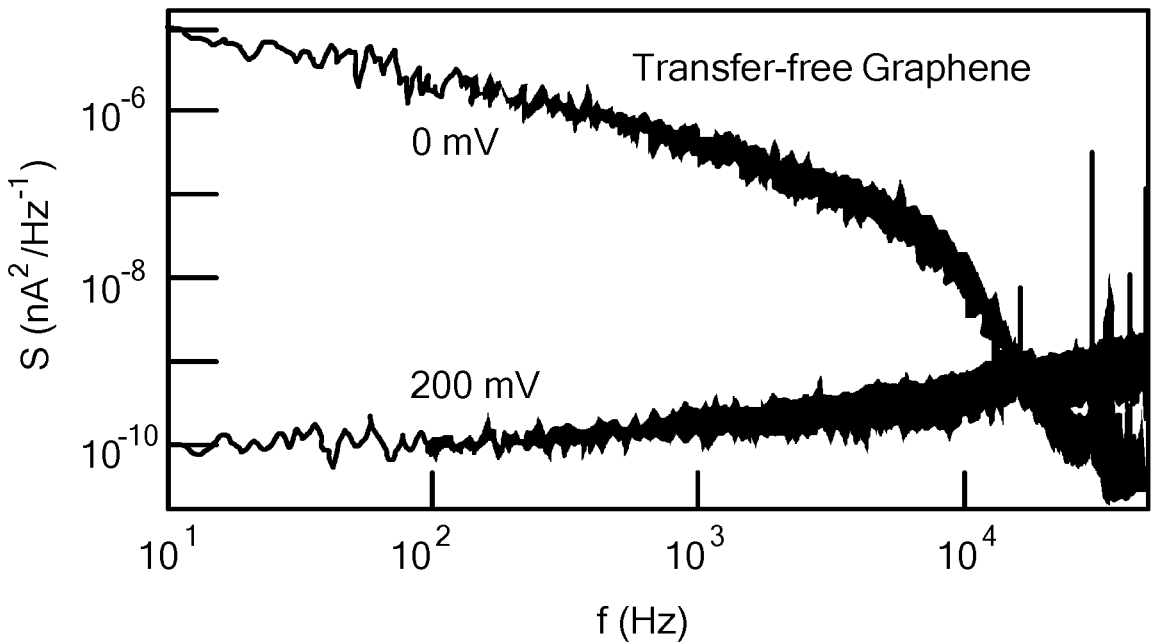
FIG. 7B shows PSD plots for an ultrathin graphene membrane containing a 7.5 nm diameter pore at 0 mV (bottom curve at left side) and 200 mV (top curve at left side) applied voltages. The graphene 1/f noise at 200 mV exceeded the MoS$_2$ noise by an order of magnitude (compare noise values at 100 Hz in FIGS. 6A and 6B).

Next, the ion-current noise exhibited by nanopores in MoS$_2$ membranes was determined and compared to that of nanopores in transfer-free graphene membrane (produced as described in WO 2015/077751, which is incorporated herein by reference). DC current values were very stable, with peak-to-peak noise values of about 400 pA at 200 kHz low pass filter setting. Power spectral density plots are shown in FIG. 7A for different applied voltages in range 0-200 mV. The pores exhibited typical 1/f noise regions that decrease with frequency until overwhelmed by capacitive noise at f>10$^4$ Hz, which is dampened using the 200 kHz digital low-pass filter (shoulders on right). The 1/f noise in the MoS$_2$ membranes was atypical of 2D pores. In comparison, graphene pores (see FIG. 7B), due to their more hydrophobic nature and charge fluctuations in the material, displayed larger 1/f current noise values than MoS$_2$.

Table 1 displays noise values for pores in membranes made of 2D materials. Heerema and co-workers, as well as Merchant and co-workers, reported for a transferred graphene pore noise density of about 10$^{-4}$ nA$^2$/Hz at a frequency of 100 Hz, whereas Waduge found for a transfer-free graphene pore a noise value of about 10$^{-5}$ nA$^2$/Hz at 200 mV. In contrast, for MoS$_2$ and SiN pores of similar conductance values and voltages, the present inventors observed noise densities at 100 Hz below 10$^{-6}$ and about 10$^{-7}$ nA$^2$/Hz, respectively. This value for the present MoS$_2$ membranes is lower than the noise reported by Feng and co-workers for a transferred MoS$_2$ pore. Recently, 1/f noise in graphene has been attributed to mechanical fluctuations in the thin material. Since lower noise levels also have been observed in transfer-free graphene than in transferred graphene, it is apparent that the even lower noise exhibited by the present polycrystalline $MoS_2$ membrane grown directly on apertures is likely a combination of superior mechanical stability afforded by the direct growth and a material-specific low noise of $MoS_2$.

TABLE 1

1/f Ionic Noise Properties For Transferred
And Direct-Growth 2D Pores

| Reference | 2D Nanopore Noise at 100 Hz, 200 mV |
|---|---|
| Hereema et al. (1) | $10^{-4}$ $nA^2$/Hz, transferred graphene |
| Merchant et al. (2) | $10^{-4}$ $nA^2$/Hz, transferred graphene |
| Waduge et al., 2014(3) | $10^{-5}$ $nA^2$/Hz, transfer-free graphene |
| Waduge et al., 2015(4) | $10^{-6}$ $nA^2$/Hz, transfer-free $MoS_2$ |
| Feng et al.(5) | $10^{-4}$ $nA^2$/Hz, transferred $MoS_2$ |

(1) Heerema, S. J.; Schneider, G. F.; Rozemuller, M.; Vicarelli, L.; Zandbergen, H. W.; Dekker, C. 1/f Noise in Graphene Nanopores. *Nanotechnology* 2015, 26, 074001.
(2) Merchant, C. A., et al. DNA Translocation through Graphene Nanopores. *Nano Lett* 2010, 10, 2915-21.
(3) Waduge, P.; Larkin, J.; Upmanyu, M.; Kar, S.; Wanunu, M. Programmed Synthesis of Freestanding Graphene Nanomembrane Arrays. *Small* 2014, 11, 597-603.
(4) Waduge, P.; Bilgin, I.; Larkin, J.; Henley, R. Y.; Goodfellow, K.; Graham, A. C.; Bell, D. C.; Vamivakas, N.; Kar, S.; Wanunu, M. Direct and Scalable Deposition of Atomically Thin Low-Noise $MoS_2$ Membranes on Apertures. *ACS Nano* 2015, 9, 7352-9.
(5) Feng, J., et al. Electrochemical Reaction in Single Layer $MoS_2$: Nanopores Opened Atom by Atom. *Nano Lett* 2015, 15, 3431-8.

Example 4. Detection of Transport of DNA Molecules Through Nanopores in $MoS_2$ Membranes The utility of the present $MoS_2$ containing nanopores in DNA transport experiments was tested by studying the transport of single-stranded DNA (ssDNA) through a $MoS_2$ pore. Rather than using TEM fabrication, for this study the recently described electrochemical reaction (ECR) process was used. [59] Briefly, a voltage of 1 V was applied for 10-15 s, after which a jump in the membrane conductance was observed, and the voltage was turned off.

Figure 8A:
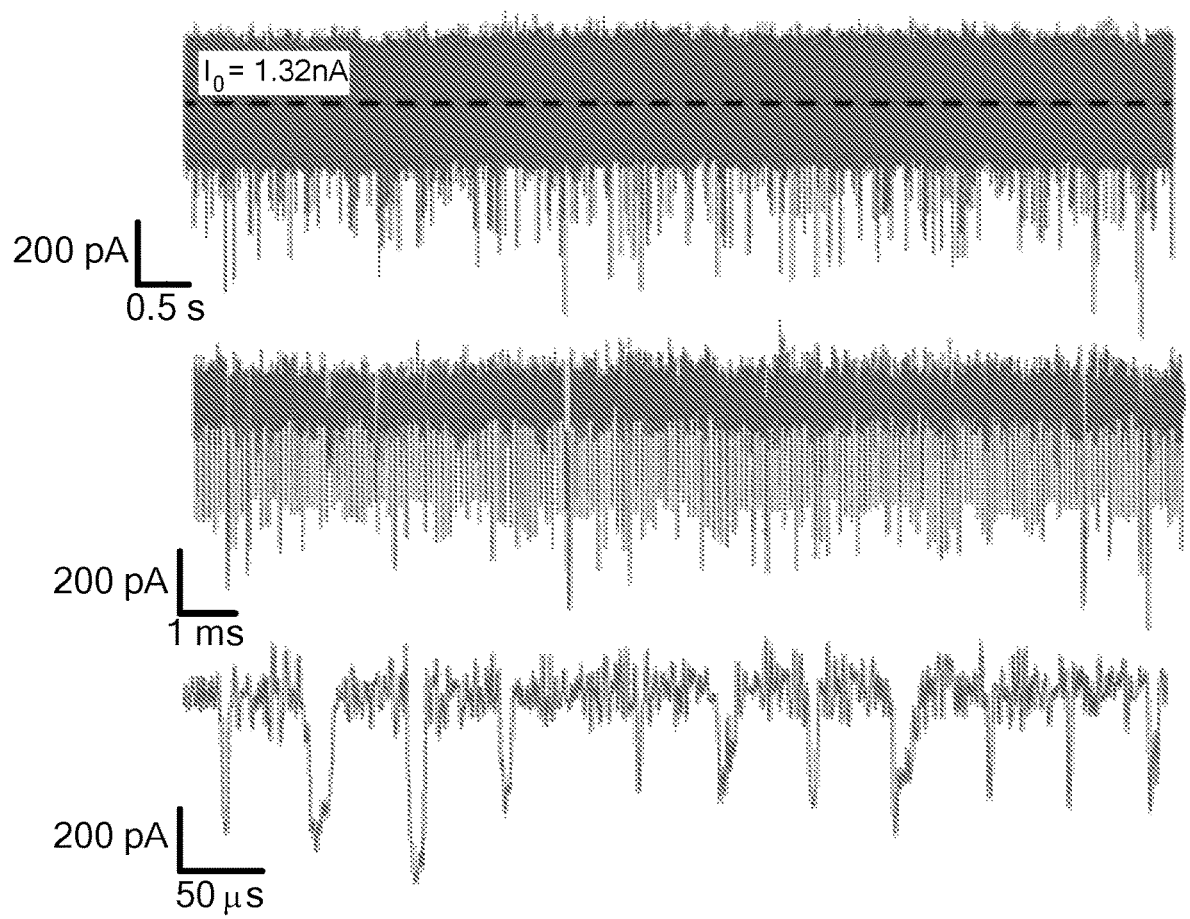
FIGS. 8A and 8B show detection of the transport of single-stranded DNA molecules through a 2.3 nm diameter MoS$_2$ nanopore.
Figure 8B:
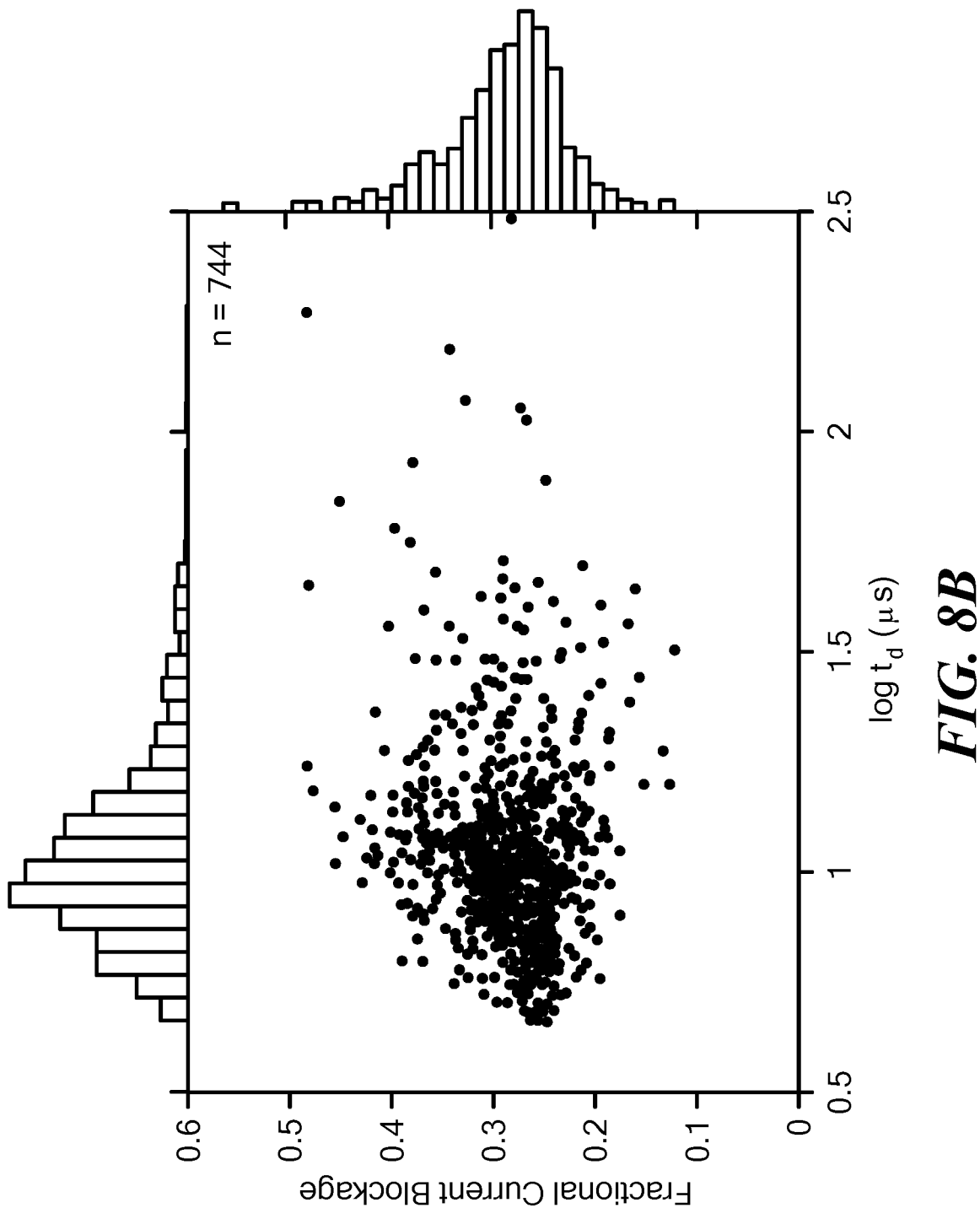
Figure 9A:
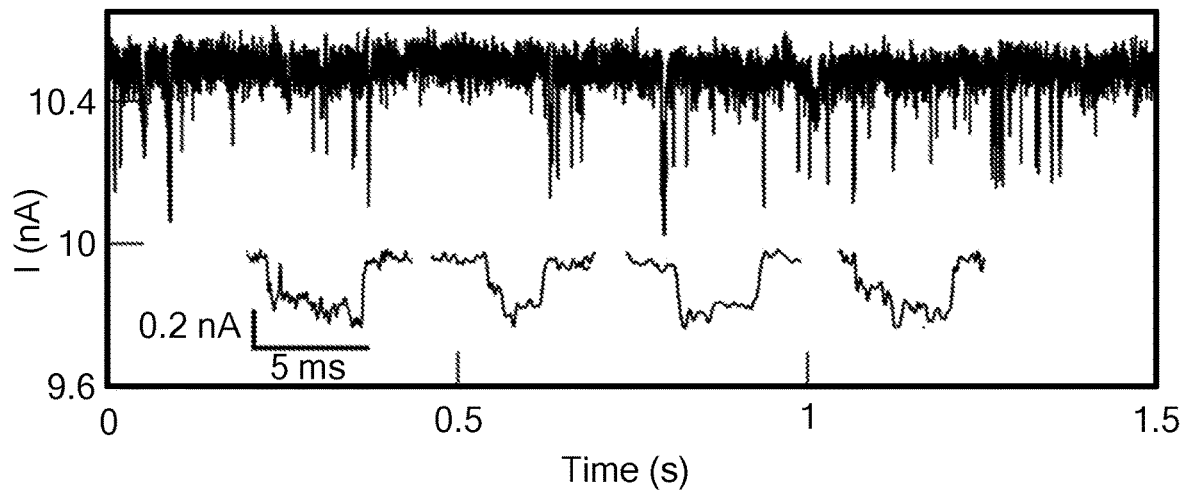
FIG. 9A shows calmodulin transport through a nanopore (22 nm diameter) in an ultra-thin MoS$_2$ membrane. A continuous 1.5 s long current trace is shown. Calmodulin was present at 100 nM in the solution, and transport of calmodulin through the nanopore can be seen as downward spikes. Bias voltage was 100 mV. Inset shows an expanded view of representative calmodulin translocation events.

After measuring a pore conductance of about 5 nS, a sample of 153-mer ssDNA was added to a total concentration of 20 nM, a 200 mV voltage was applied, and current traces were recorded. A sample 3-s current trace is shown in FIG. 9A, which displays a stochastic set of downward current pulses, each indicating the transport of an individual DNA molecule through the pore. Below the continuous current trace in FIG. 8A are shown concatenated sets of events that were analyzed using Python software. In FIG. 8B is shown a scatter plot of the fractional current blockade (defined as the ratio of the spike mean amplitude to the open pore current) vs. dwell time for the 744 events in the experiment. Because of the 200 kHz bandwidth, events below 3 µs are significantly distorted and therefore were discarded from the analysis. Histograms of both parameters are also shown above and to the right of the scatter plots, from which mean dwell time was determined as 16 µs and mean fractional current blockade as 26%. On the basis of the values of the open pore current (1.32 nA at 200 mV) and the mean blockade values, the effective pore diameter and thickness were estimated as 2.3 nm and two $MoS_2$ layers (1.6 nm), respectively. Given the relatively large pore size as compared with the nominal diameter of ssDNA (about 1.3 nm), the mean transport velocity of 0.1 µs/bp is reasonable and in accordance with a prior study. [60]

Finally, the data in FIG. 8B shows many events with dwell times ($t_d$) below 10 µs, which makes their detection challenging. However, because the mean capture rate was 0.95 $s^{-1}$ $nM^{-1}$ in the present experiment, and a mean capture rate of 0.02 $s^{-1}$ $nM^{-1}$ was obtained for a 1.7 nm diameter $HfO_2$ pore under similar conditions, [61] it is concluded that DNA capture is efficient in a $MoS_2$ pore.

Figure 9B:
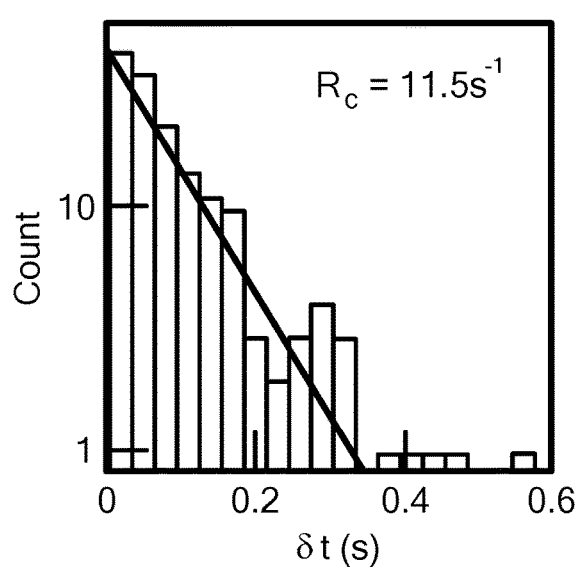
FIG. 9B shows a histogram of time intervals between events. The capture rate (Rc) of calmodulin translocations is shown in the legend, which is the inverse of the time constant of the time interval distribution (solid diagonal line).
Figure 9C:
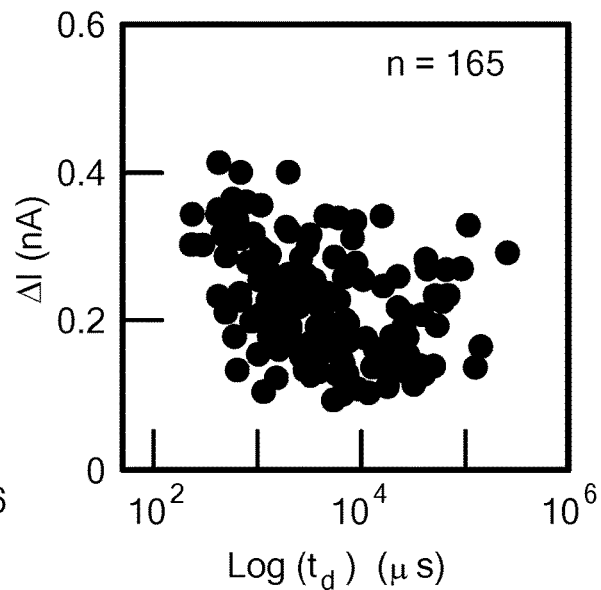
FIG. 9C shows a scatter plot of the magnitude of current blockades vs. dwell time for 165 calmodulin translocation events (sampling rate=4.2 MHz, low-pass filtered at 50 kHz, T=25° C., 0.4 M KCl, pH 7.8).

Example 5. Detection of Transport of Protein Molecules Through Nanopores in $MoS_2$ Membranes Calmodulin transport was measured through an ultrathin $MoS_2$ membrane containing a nanopore. The methodology was similar to that used in Example 4 to observe ssDNA transport, except that a larger pore diameter of 22 nm was used. FIG. 9A shows a continuous 1.5 s long current vs. time trace for the transport of 100 nM calmodulin through the 22 nm-diameter $MoS_2$ nanopore at 100 mV bias voltage applied at the trans side. Downward spikes correspond to the translocation or interaction of calmodulin with the pore. The inset shows an expanded view of representative events. FIG. 9B shows a histogram of time intervals between events. The capture rate ($R_c$) of calmodulin translocations is shown in the legend, which is the inverse of the time constant of the time interval distribution (solid line). FIG. 9C shows a scatter plot of current blockades vs. dwell times for 165 calmodulin translocation events (sampling rate=4.2 MHz, low-pass filtered at 50 kHz, T=25° C., 0.4 M KCl, pH 7.8).

Figure 4B:
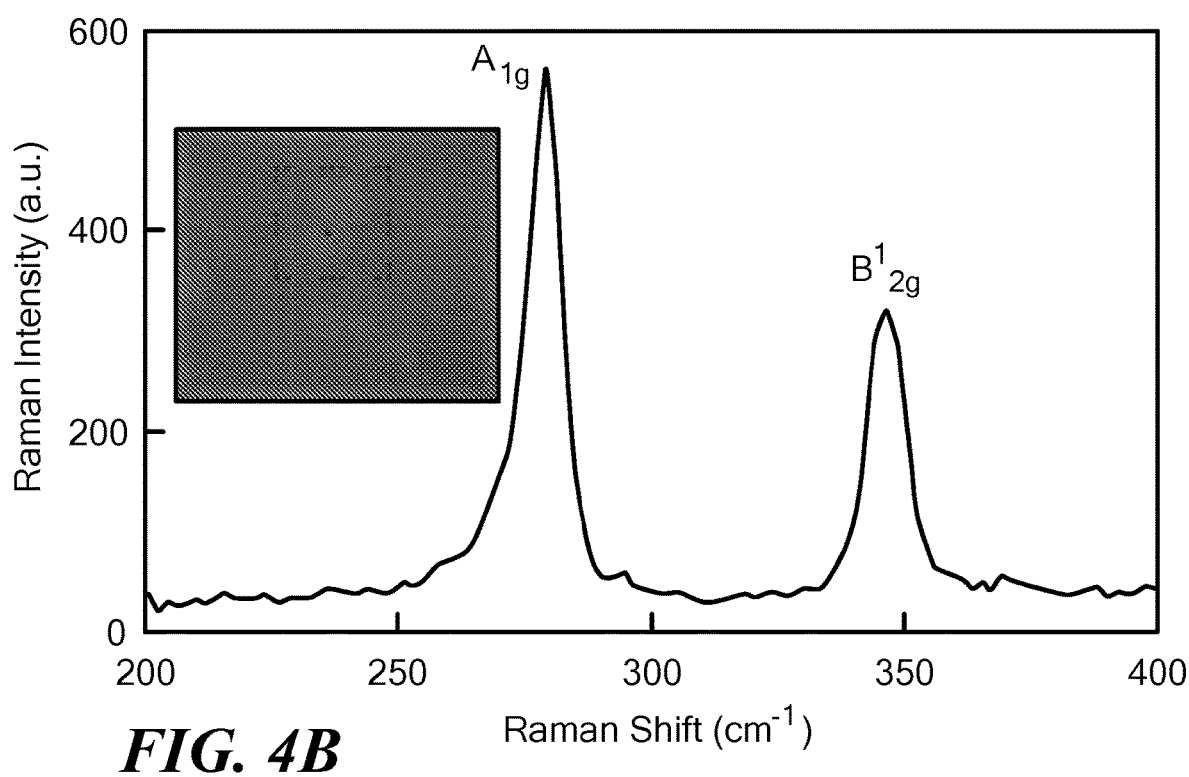
FIG. 4B shows a Raman spectrum of a molybdenum diselenide ($MoSe_2$) membrane grown on the aperture shown inside the dashed line box of the inset. The Raman spectrum was collected in from the area inside the box. The inset shows an optical image of the $MoSe_2$ membrane deposited on an aperture-containing freestanding SiN sheet.
Figure 5:
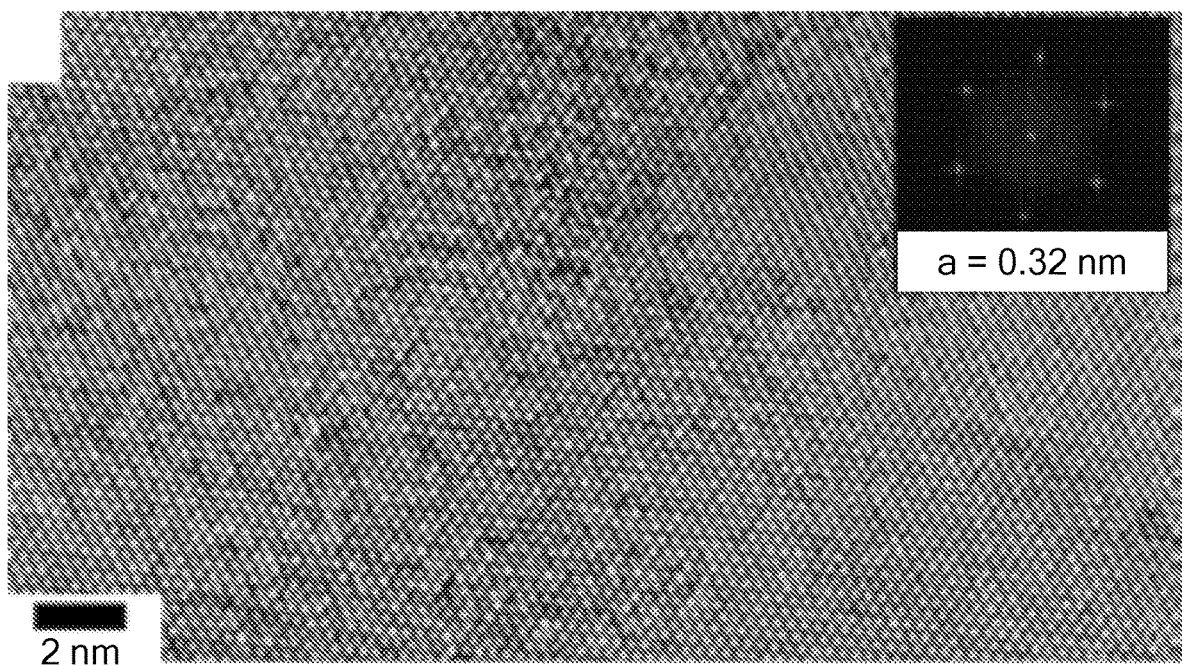
FIG. 5 shows an atomic resolution image of a freestanding 10 nm×20 nm region of a $MoS_2$ membrane. The inset shows the FFT spectrum of the image.

Example 6. Fabrication of $MoSe_2$ Membrane 6 mg of Se powder was added to one of the quartz boats and 2 mg of $MoO_2$ powder to the other boat. The Se boat was placed in the upstream region of the furnace while the $MoO_2$ boat was kept in the center of the furnace. The furnace was purged with 10 sccm $H_2$ for 30 min and then the temperature of the furnace was raised to 300° C. at a rate of 15° C./min under flow of 125 sccm Ar. The furnace was held at 300° C. for 10 min and then raised to 650° C. at a rate of 5° C./min. The furnace was held at 650° C. for 30 min, and then the hood of the furnace was opened and and the system allowed to cool to room temperature after 30 min under the flow of 10 sccm $H_2$ and 125 sccm Ar. FIG. 4B shows Raman characterization of the $MoSe_2$ membrane.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

REFERENCES

[1] K. S. Novoselov, D. Jiang, F. Schedin, T. J. Booth, V. V. Khotkevich, S. V. Morozov, A. K. Geim, Proceedings of the National Academy of Sciences of the United States of America, 102 (2005) 10451-10453.
[2] F. Schwierz, Nature nanotechnology, 6 (2011) 135-136.
[3] K. Novoselov, Nature materials, 6 (2007) 720-721.
[4] F. Traversi, C. Railton, S. M. Benameur, K. Liu, S. Khlybov, M. Tosun, D. Krasnozhon, A. Kis, A. Radenovic, Nature nanotechnology, 8 (2013) 939-945.

[5] B. K. Bradovic, R.; Heinz, F.; Matagne, P.; Rakshit, T.; Giles, M. D.; Stettler, M. A.; Nikonov, D. E., Appl. Phys. Lett., 88 (2006) 142102.
[6] R. Ganatra, Q. Zhang, ACS nano, 8 (2014) 4074-4099.
[7] W. Ho, J. C. Yu, J. Lin, J. Yu, P. Li, Langmuir, 20 (2004) 5865-5869.
[8] E. Gourmelon, O. Lignier, H. Hadouda, G. Couturier, J. Bernede, J. Tedd, J. Pouzet, J. Salardenne, Solar energy materials and solar cells, 46 (1997) 115-121.
[9] K. F. Mak, C. Lee, J. Hone, J. Shan, T. F. Heinz, Physical review letters, 105 (2010) 136805.
[10] G. Eda, H. Yamaguchi, D. Voiry, T. Fujita, M. Chen, M. Chhowalla, Nano letters, 11 (2011) 5111-5116.
[11] B. Radisavljevic, A. Radenovic, J. Brivio, V. Giacometti, A. Kis, Nature nanotechnology, 6 (2011) 147-150.
[12] A. Splendiani, L. Sun, Y. Zhang, T. Li, J. Kim, C. Y. Chim, G. Galli, F. Wang, Nano letters, 10 (2010) 1271-1275.
[13] A. Kuc, N. Zibouche, T. Heine, Physical Review B, 83 (2011) 245213.
[14] Y. Liu, H. Nan, X. Wu, W. Pan, W. Wang, J. Bai, W. Zhao, L. Sun, X. Wang, Z. Ni, ACS nano, 7 (2013) 4202-4209.
[15] A. Castellanos-Gomez, R. Roldan, E. Cappelluti, M. Buscema, F. Guinea, H. S. van der Zant, G. A. Steele, Nano letters, 13 (2013) 5361-5366.
[16] Z. Yin, H. Li, H. Li, L. Jiang, Y. Shi, Y. Sun, G. Lu, Q. Zhang, X. Chen, H. Zhang, ACS nano, 6 (2011) 74-80.
[17] H. S. Lee, S. W. Min, Y. G. Chang, M. K. Park, T. Nam, H. Kim, J. H. Kim, S. Ryu, S. Im, Nano letters, 12 (2012) 3695-3700.
[18] J. Feng, X. Qian, C.-W. Huang, J. Li, Nature Photonics, 6 (2012) 866-872.
[19] A. Carladous, R. Coratger, F. Ajustron, G. Seine, R. Péchou, J. Beauvillain, Physical Review B, 66 (2002) 045401.
[20] D. Sercombe, S. Schwarz, O. Del Pozo-Zamudio, F. Liu, B. J. Robinson, E. A. Chekhovich, Tartakovskii, II, O. Kolosov, A. I. Tartakovskii, Scientific reports, 3 (2013) 3489.
[21] A. Castellanos-Gomez, M. Poot, G. A. Steele, H. S. van der Zant, N. Agrait, G. Rubio-Bollinger, Advanced materials, 24 (2012) 772-775.
[22] L. Sun, H. Huang, X. Peng, Chemical communications, 49 (2013) 10718-10720.
[23] S. Bertolazzi, J. Brivio, A. Kis, ACS nano, 5 (2011) 9703-9709.
[24] A. Ayari, E. Cobas, O. Ogundadegbe, M. S. Fuhrer, Journal of applied physics, 101 (2007) 014507-014507-014505.
[25] V. Podzorov, M. Gershenson, C. Kloc, R. Zeis, E. Bucher, Applied Physics Letters, 84 (2004) 3301-3303.
[26] A. Kis, D. Mihailovic, M. Remskar, A. Mrzel, A. Jesih, I. Piwonski, A. J. Kulik, W. Benoît, L. Forró, Advanced materials, 15 (2003) 733-736.
[27] B. Radisavljevic, M. B. Whitwick, A. Kis, ACS nano, 5 (2011) 9934-9938.
[28] H. Wang, L. Yu, Y. H. Lee, Y. Shi, A. Hsu, M. L. Chin, L. J. Li, M. Dubey, J. Kong, T. Palacios, Nano letters, 12 (2012) 4674-4680.
[29] C. Zhu, G. Yang, H. Li, D. Du, Y. Lin, Analytical chemistry, (2014).
[30] J. Z. Ou, A. F. Chrimes, Y. Wang, S. Y. Tang, M. S. Strano, K. Kalantar-zadeh, Nano letters, 14 (2014) 857-863.
[31] T. Wang, R. Zhu, J. Zhuo, Z. Zhu, Y. Shao, M. Li, Analytical chemistry, 86 (2014) 12064-12069.
[32] T. Wang, H. Zhu, J. Zhuo, Z. Zhu, P. Papakonstantinou, G. Lubarsky, J. Lin, M. Li, Analytical chemistry, 85 (2013) 10289-10295.
[33] D. Sarkar, W. Liu, X. Xie, A. C. Anselmo, S. Mitragotri, K. Banerjee, ACS nano, 8 (2014) 3992-4003.
[34] S. Balendhran, S. Walia, M. Alsaif, E. P. Nguyen, J. Z. Ou, S. Zhuiykov, S. Sriram, M. Bhaskaran, K. Kalantar-Zadeh, ACS nano, 7 (2013) 9753-9760.
[35] K. K. Saha, M. Drndic, B. K. Nikolic, Nano letters, 12 (2012) 50-55.
[36] J. Prasongkit, A. Grigoriev, B. Pathak, R. Ahuja, R. H. Scheicher, Nano letters, 11 (2011) 1941-1945.
[37] S. Banerjee, J. Shim, J. Rivera, X. Jin, D. Estrada, V. Solovyeva, X. You, J. Pak, E. Pop, N. Aluru, R. Bashir, ACS nano, 7 (2013) 834-843.
[38] S. Garaj, W. Hubbard, A. Reina, J. Kong, D. Branton, J. A. Golovchenko, Nature, 467 (2010) 190-193.
[39] G. F. Schneider, S. W. Kowalczyk, V. E. Calado, G. Pandraud, H. W. Zandbergen, L. M. Vandersypen, C. Dekker, Nano letters, 10 (2010) 3163-3167.
[40] C. A. Merchant, K. Healy, M. Wanunu, V. Ray, N. Peterman, J. Bartel, M. D. Fischbein, K. Venta, Z. Luo, A. T. Johnson, M. Drndic, Nano letters, 10 (2010) 2915-2921.
[41] P. Waduge, J. Larkin, M. Upmanyu, S. Kar, M. Wanunu, Small, (2014).
[42] K. Liu, J. Feng, A. Kis, A. Radenovic, ACS nano, 8 (2014) 2504-2511.
[43] A. B. Farimani, K. Min, N. R. Aluru, ACS nano, 8 (2014) 7914-7922.
[44] S. Liu, B. Lu, Q. Zhao, J. Li, T. Gao, Y. Chen, Y. Zhang, Z. Liu, Z. Fan, F. Yang, L. You, D. Yu, Advanced materials, 25 (2013) 4549-4554.
[45] P. Joensen, R. Frindt, S. R. Morrison, Materials research bulletin, 21 (1986) 457-461.
[46] M. B. Dines, Journal of Chemical Education, 51 (1974) 221.
[47] J. N. Coleman, M. Lotya, A. O'Neill, S. D. Bergin, P. J. King, U. Khan, K. Young, A. Gaucher, S. De, R. J. Smith, I. V. Shvets, S. K. Arora, G. Stanton, H. Y. Kim, K. Lee, G. T. Kim, G. S. Duesberg, T. Hallam, J. J. Boland, J. J. Wang, J. F. Donegan, J. C. Grunlan, G. Moriarty, A. Shmeliov, R. J. Nicholls, J. M. Perkins, E. M. Grieveson, K. Theuwissen, D. W. McComb, P. D. Nellist, V. Nicolosi, Science, 331 (2011) 568-571.
[48] X. Wang, H. Feng, Y. Wu, L. Jiao, Journal of the American Chemical Society, 135 (2013) 5304-5307.
[49] Y. H. Lee, X. Q. Zhang, W. Zhang, M. T. Chang, C. T. Lin, K. D. Chang, Y. C. Yu, J. T. Wang, C. S. Chang, L. J. Li, T. W. Lin, Advanced materials, 24 (2012) 2320-2325.
[50] X. Ling, Y. H. Lee, Y. Lin, W. Fang, L. Yu, M. S. Dresselhaus, J. Kong, Nano letters, 14 (2014) 464-472.
[51] J. K. Huang, J. Pu, C. L. Hsu, M. H. Chiu, Z. Y. Juang, Y. H. Chang, W. H. Chang, Y. Iwasa, T. Takenobu, L. J. Li, ACS nano, 8 (2014) 923-930.
[52] Y. H. Lee, L. Yu, H. Wang, W. Fang, X. Ling, Y. Shi, C. T. Lin, J. K. Huang, M. T. Chang, C. S. Chang, M. Dresselhaus, T. Palacios, L. J. Li, J. Kong, Nano letters, 13 (2013) 1852-1857.
[53] W. Zhang, J. K. Huang, C. H. Chen, Y. H. Chang, Y. J. Cheng, L. J. Li, Advanced materials, 25 (2013) 3456-3461.
[54] S. Najmaei, Z. Liu, W. Zhou, X. Zou, G. Shi, S. Lei, B. I. Yakobson, J. C. Idrobo, P. M. Ajayan, J. Lou, Nature materials, 12 (2013) 754-759.

[55] C. Ataca, M. Topsakal, E. Akturk, S. Ciraci, The Journal of Physical Chemistry C, 115 (2011) 16354-16361.
[56] Y. Zhao, X. Luo, H. Li, J. Zhang, P. T. Araujo, C. K. Gan, J. Wu, H. Zhang, S. Y. Quek, M. S. Dresselhaus, Nano letters, 13 (2013) 1007-1015.
[57] S. Sahoo, A. P. Gaur, M. Ahmadi, M. J.-F. Guinel, R. S. Katiyar, The Journal of Physical Chemistry C, 117 (2013) 9042-9047.
[58] C. Lee, H. Yan, L. E. Brus, T. F. Heinz, J. Hone, S. Ryu, ACS nano, 4 (2010) 2695-2700.
[59] 8. Feng, J.; Liu, K.; Graf, M.; Lihter, M.; Bulushev, R. D.; Dumcenco, D.; Alexander, D. T. L.; Krasnozhon, D.; Vuletic, T.; Kis, A.; et al., Nano Lett. 2015, 15,3431-8.
[60] McNally, B.; Wanunu, M.; Meller, A. Electromechanical Unzipping of Individual DNA Molecules using Synthetic Sub-2 nm Pores. Nano Lett. 2008, 8, 3418-3422.
[61] Larkin, J.; Henley, R.; Bell, D. C.; Cohen-Karni, T.; Rosenstein, J. K.; Wanunu, M. Slow DNA Transport through Nanopores in Hafnium Oxide Membranes. ACS Nano 2013, 7, 10121-10128.

What is claimed is:

1. A method of fabricating an ultrathin membrane comprising a two-dimensional material, the membrane spanning an aperture in a sheet of solid state material and attached to a surface of the sheet in an area surrounding the aperture, the method comprising the step of performing chemical vapor deposition of a first membrane precursor disposed on a first side of a sheet of solid state material comprising an aperture and a second membrane precursor disposed on a second side of the sheet, opposite the first side, whereby the first and second precursors are heated to promote sublimation prior to said deposition and said ultrathin membrane is formed from the first and second precursors across the aperture and contacting a surface of the sheet of solid state material in an area surrounding the aperture.

2. The method of claim 1, wherein the first membrane precursor comprises a metal selected from the group consisting of Ga, In, Hf, Mo, Nb, Ni, Pd, Pt, Re, Ta, Ti, W, and Zr.

3. The method of claim 2, wherein the first membrane precursor is an oxide of said metal.

4. The method of claim 3, wherein atoms of the second membrane precursor displace oxygen atoms of the oxide and form a two-dimensional material at the aperture.

5. The method of claim 1, wherein the second membrane precursor comprises S, Se, or Te.

6. The method of claim 1, wherein the two-dimensional material formed is selected from the group consisting of GaS, GaSe, InS, InSe, $HfS_2$, $HfSe_2$, $HfTe_2$, $MoS_2$, $MoSe_2$, $MoTe_2$, $NbS_2$, $NbSe_2$, $NbTe_2$, $NiS_2$, $NiSe_2$, $NiTe_2$, $PdS_2$, $PdSe_2$, $PdTe_2$, $PtS_2$, $PtSe_2$, $PtTe_2$, $ReS_2$, $ReSe_2$, $ReTe_2$, $TaS_2$, $TaSe_2$, $TaTe_2$, $TiS_2$, $TiSe_2$, $TiTe_2$, $WS_2$, $WSe_2$, $WTe_2$, $ZrS_2$, $ZrSe_2$, and $ZrTe_2$.

7. The method of claim 6, wherein the two-dimensional material consists essentially of $MoS_2$ or $MoSe_2$.

8. The method of claim 1, wherein said chemical vapor deposition comprises heating the first membrane precursor and second membrane precursor in separate containers and in the presence of an inert carrier gas.

9. The method of claim 8, wherein the container comprising the first membrane precursor is disposed near the first side of said sheet of solid state material, the container comprising the second membrane precursor is disposed remotely from said sheet of solid state material, and the heated second membrane precursor is carried towards the aperture by the carrier gas at the second side of said sheet of solid state material; and wherein the ultrathin membrane is fabricated on a surface of the sheet on the second side.

10. The method of claim 8, wherein said inert carrier gas is Ar or $N_2$.

11. The method of claim 1, wherein the first and second membrane precursors are heated to about 650 to 800° C. at about 3 to 10° C./min under carrier gas flow, and held at about 650 to 800° C. for about 15 to 60 minutes.

12. The method of claim 11 wherein, prior to said heating step, the first and second membrane precursors are heated to about 300 to 400° C. at a rate of about 20 to 30° C./min under carrier gas flow and held at about 300 to 400° C. for about 15 to 30 minutes, and wherein the two-dimensional material formed is $MoS_2$.

13. The method of claim 1, wherein said carrier gas flow is maintained at a rate of about 180 to 200 sccm.

14. The method of claim 1, wherein the ultrathin membrane is fabricated across an aperture having a diameter of from about 0.02 µm to about 2.0 µm.

15. The method of claim 1, wherein the solid state material is a material selected from the group consisting of silicon nitride, silicon dioxide, hafnium dioxide, titanium dioxide, and aluminum oxide.

16. The method of claim 1, wherein the thickness of the ultrathin membrane is 1-2 atomic layers.

17. The method of claim 1, wherein the ultrathin membrane is essentially free of holes and atomic vacancies.

18. The method of claim 1, wherein the ultrathin membrane consists essentially of monocrystalline $MoS_2$ or $MoSe_2$.

19. The method of claim 1, further comprising the step of forming one or more nanopores in the ultrathin membrane.

20. The method of claim 19, wherein the one or more nanopores are formed using an electron beam, an ion beam, a laser, or application of voltage across the membrane.

21. The method of claim 19, wherein the one or more nanopores each have a diameter in the range from about 0.3 nm to about 50 nm.

* * * * *